US008851355B2

(12) United States Patent
Aranyi et al.

(10) Patent No.: US 8,851,355 B2
(45) **Date of Patent: *Oct. 7, 2014**

(54) APPARATUS FOR ENDOSCOPIC PROCEDURES

(71) Applicant: Covidien LP, Mansfield, MA (US)

(72) Inventors: Ernest Aranyi, Easton, CT (US); Dwight Bronson, Cheshire, CT (US); David Racenet, Killingworth, CT (US)

(73) Assignee: Covidien LP, Mansfield, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/169,441

(22) Filed: Jan. 31, 2014

(65) Prior Publication Data

US 2014/0144970 A1 May 29, 2014

Related U.S. Application Data

(63) Continuation of application No. 13/444,228, filed on Apr. 11, 2012, now Pat. No. 8,672,206, which is a continuation-in-part of application No. 13/280,898, filed on Oct. 25, 2011, which is a continuation-in-part of application No. 13/280,859, filed on Oct. 25, 2011, now Pat. No. 8,657,177.

(51) Int. Cl.

| | |
|---|---|
| ***A61B 17/068*** | (2006.01) |
| ***A61B 17/072*** | (2006.01) |
| *A61B 17/00* | (2006.01) |
| *A61B 19/00* | (2006.01) |
| *A61B 17/04* | (2006.01) |
| *A61B 17/29* | (2006.01) |

(52) U.S. Cl.

CPC ..... *A61B 17/068* (2013.01); *A61B 2017/00323* (2013.01); *A61B 2019/446* (2013.01); *A61B 17/07292* (2013.01); *A61B 2017/00398* (2013.01); *A61B 17/0483* (2013.01); *A61B 2017/00734* (2013.01); *A61B 2017/00314* (2013.01); *A61B 2017/07278* (2013.01); *A61B 17/07207* (2013.01); *A61B 2017/00473* (2013.01); *A61B 2017/294* (2013.01); *A61B 2017/00685* (2013.01)

USPC ..... 227/176.1; 227/19; 227/175.2; 227/180.1

(58) Field of Classification Search

USPC ............... 227/19, 175.1, 175.2, 176.1, 178.1, 227/180.1; 606/139, 153, 219

See application file for complete search history.

(56) References Cited

U.S. PATENT DOCUMENTS

| | | | |
|---|---|---|---|
| 2,777,340 | A | 1/1957 | Hettwer et al. |
| 2,957,353 | A | 10/1960 | Babacz |

(Continued)

FOREIGN PATENT DOCUMENTS

| | | | |
|---|---|---|---|
| CA | 2451558 | A1 | 1/2003 |
| CN | 102247182 | A | 11/2011 |

(Continued)

OTHER PUBLICATIONS

International Search Report corresponding to PCT/US2005/027266, completed May 30, 2008 and mailed Jun. 18, 2008; (2 pp.).

(Continued)

*Primary Examiner* — Scott A. Smith

(57) ABSTRACT

A surgical system has a jaw assembly including a plurality of fasteners, an anvil and a drive beam for pushing an actuation sled. A drive screw imparts motion to the drive beam. An elongated body is configured to connect with the jaw assembly. A drive link connects a flexible drive shaft to the drive screw, the drive link being disposed off-axis. The jaw assembly and elongated body are separable from each other.

20 Claims, 30 Drawing Sheets

(56) References Cited

U.S. PATENT DOCUMENTS 3,111,328 A 11/1963 Di Rito et al.
3,695,058 A 10/1972 Keith, Jr.
3,734,515 A 5/1973 Dudek
3,759,336 A 9/1973 Marcovitz et al.
4,162,399 A 7/1979 Hudson
4,606,343 A 8/1986 Conta et al.
4,705,038 A 11/1987 Sjostrom et al.
4,874,181 A 10/1989 Hsu
5,129,118 A 7/1992 Walmesley
5,129,570 A 7/1992 Schulze et al.
5,152,744 A 10/1992 Krause et al.
5,312,023 A 5/1994 Green et al.
5,326,013 A 7/1994 Green et al.
5,350,355 A 9/1994 Sklar
5,383,874 A 1/1995 Jackson et al.
5,383,880 A 1/1995 Hooven
5,389,098 A 2/1995 Tsuruta et al.
5,395,033 A 3/1995 Byrne et al.
5,400,267 A 3/1995 Denen et al.
5,413,267 A 5/1995 Solyntjes et al.
5,467,911 A 11/1995 Tsuruta et al.
5,476,379 A 12/1995 Disel
5,487,499 A 1/1996 Sorrentino et al.
5,518,163 A 5/1996 Hooven
5,518,164 A 5/1996 Hooven
5,526,822 A 6/1996 Burbank et al.
5,529,235 A 6/1996 Boiarski et al.
5,535,934 A 7/1996 Boiarski et al.
5,535,937 A 7/1996 Boiarski et al.
5,542,594 A 8/1996 McKean et al.
5,562,239 A 10/1996 Boiarski et al.
5,653,374 A 8/1997 Young et al.
5,667,517 A 9/1997 Hooven
5,693,042 A 12/1997 Boiarski et al.
5,704,534 A 1/1998 Huitema et al.
5,713,505 A 2/1998 Huitema
5,779,130 A 7/1998 Alesi et al.
5,782,396 A * 7/1998 Mastri et al. ............... 227/175.3
5,782,397 A 7/1998 Koukline
5,820,009 A 10/1998 Melling et al.
5,863,159 A 1/1999 Lasko
5,908,427 A 6/1999 McKean et al.
5,954,259 A 9/1999 Viola et al.
5,964,774 A 10/1999 McKean et al.
5,993,454 A 11/1999 Longo
6,017,354 A 1/2000 Culp et al.
6,032,849 A * 3/2000 Mastri et al. ............... 227/176.1
6,045,560 A 4/2000 McKean et al.
6,090,123 A 7/2000 Culp et al.
6,129,547 A 10/2000 Cise et al.
6,241,139 B1 * 6/2001 Milliman et al. .......... 227/175.1
6,264,087 B1 7/2001 Whitman
6,302,311 B1 10/2001 Adams et al.
6,315,184 B1 11/2001 Whitman
6,321,855 B1 11/2001 Barnes
6,329,778 B1 12/2001 Culp et al.
6,343,731 B1 2/2002 Adams et al.
6,348,061 B1 2/2002 Whitman
6,368,324 B1 4/2002 Dinger et al.
6,434,507 B1 8/2002 Clayton et al.
6,443,973 B1 9/2002 Whitman
6,461,372 B1 10/2002 Jensen et al.
6,488,197 B1 12/2002 Whitman
6,491,201 B1 12/2002 Whitman
6,533,157 B1 3/2003 Whitman
6,537,280 B2 3/2003 Dinger et al.
6,610,066 B2 8/2003 Dinger et al.
6,611,793 B1 8/2003 Burnside et al.
6,698,643 B2 3/2004 Whitman
6,699,177 B1 3/2004 Wang et al.
6,716,233 B1 4/2004 Whitman
6,792,390 B1 9/2004 Burnside et al.
6,817,508 B1 11/2004 Racenet et al.
6,846,308 B2 1/2005 Whitman et al.
6,846,309 B2 1/2005 Whitman et al.
6,849,071 B2 2/2005 Whitman et al.
6,959,852 B2 11/2005 Shelton, IV et al.
6,964,363 B2 11/2005 Wales et al.
6,981,628 B2 1/2006 Wales
6,981,941 B2 1/2006 Whitman et al.
6,986,451 B1 * 1/2006 Mastri et al. ............... 227/176.1
7,032,798 B2 4/2006 Whitman et al.
7,055,731 B2 6/2006 Shelton, IV et al.
7,077,856 B2 7/2006 Whitman
7,111,769 B2 9/2006 Wales et al.
7,143,923 B2 12/2006 Shelton, IV et al.
7,143,925 B2 12/2006 Shelton, IV et al.
7,143,926 B2 12/2006 Shelton, IV et al.
7,147,138 B2 12/2006 Shelton, IV
7,225,964 B2 * 6/2007 Mastri et al. ............... 227/176.1
7,246,734 B2 7/2007 Shelton, IV
7,328,828 B2 2/2008 Ortiz et al.
7,364,061 B2 4/2008 Swayze et al.
7,380,695 B2 6/2008 Doll et al.
7,380,696 B2 6/2008 Shelton, IV et al.
7,404,508 B2 7/2008 Smith et al.
7,407,078 B2 * 8/2008 Shelton et al. ............. 227/180.1
7,416,101 B2 8/2008 Shelton, IV et al.
7,419,080 B2 9/2008 Smith et al.
7,422,139 B2 9/2008 Shelton, IV et al.
7,431,189 B2 10/2008 Shelton, IV et al.
7,441,684 B2 10/2008 Shelton, IV et al.
7,448,525 B2 11/2008 Shelton, IV et al.
7,464,846 B2 12/2008 Shelton, IV et al.
7,464,847 B2 12/2008 Viola et al.
7,464,849 B2 12/2008 Shelton, IV et al.
7,481,347 B2 1/2009 Roy
7,487,899 B2 2/2009 Shelton, IV et al.
7,549,564 B2 6/2009 Boudreaux
7,565,993 B2 * 7/2009 Milliman et al. .......... 227/175.1
7,568,603 B2 8/2009 Shelton, IV et al.
7,588,176 B2 9/2009 Timm et al.
7,637,409 B2 12/2009 Marczyk
7,641,093 B2 1/2010 Doll et al.
7,644,848 B2 1/2010 Swayze et al.
7,670,334 B2 3/2010 Hueil et al.
7,673,780 B2 3/2010 Shelton, IV et al.
7,721,931 B2 5/2010 Shelton, IV et al.
7,740,159 B2 6/2010 Shelton, IV et al.
7,743,960 B2 6/2010 Whitman et al.
7,758,613 B2 7/2010 Whitman
7,766,210 B2 8/2010 Shelton, IV et al.
7,770,773 B2 8/2010 Whitman et al.
7,770,775 B2 8/2010 Shelton, IV et al.
7,793,812 B2 * 9/2010 Moore et al. ............... 227/176.1
7,799,039 B2 9/2010 Shelton, IV et al.
7,802,712 B2 9/2010 Milliman et al.
7,845,537 B2 12/2010 Shelton, IV et al.
7,857,185 B2 * 12/2010 Swayze et al. ............. 227/175.2
7,905,897 B2 3/2011 Whitman et al.
7,918,230 B2 4/2011 Whitman et al.
7,947,034 B2 5/2011 Whitman
7,951,071 B2 5/2011 Whitman et al.
7,959,051 B2 * 6/2011 Smith et al. ................ 227/176.1
7,963,433 B2 6/2011 Whitman et al.
7,967,178 B2 6/2011 Scirica et al.
7,992,758 B2 8/2011 Whitman et al.
8,016,855 B2 9/2011 Whitman et al.
8,020,743 B2 9/2011 Shelton, IV
8,114,118 B2 2/2012 Knodel et al.
8,157,151 B2 4/2012 Ingmanson et al.
8,182,494 B1 5/2012 Yencho et al.
8,186,555 B2 5/2012 Shelton, IV et al.
8,220,367 B2 7/2012 Hsu
8,241,322 B2 8/2012 Whitman et al.
8,292,150 B2 10/2012 Bryant
8,292,888 B2 10/2012 Whitman
8,357,144 B2 1/2013 Whitman et al.
8,365,972 B2 2/2013 Aranyi et al.
8,372,057 B2 2/2013 Cude et al.
8,391,957 B2 3/2013 Carlson et al.
8,517,241 B2 8/2013 Nicholas et al.
8,657,177 B2 2/2014 Scirica et al.
8,672,206 B2 3/2014 Aranyi et al.

(56) References Cited

U.S. PATENT DOCUMENTS

| | | | |
|---|---|---|---|
| 2004/0111012 | A1 | 6/2004 | Whitman |
| 2006/0142656 | A1 | 6/2006 | Malackowski et al. |
| 2006/0278680 | A1 | 12/2006 | Viola et al. |
| 2007/0023477 | A1 | 2/2007 | Whitman et al. |
| 2007/0029363 | A1 | 2/2007 | Popov |
| 2007/0055219 | A1 | 3/2007 | Whitman et al. |
| 2007/0084897 | A1 | 4/2007 | Shelton et al. |
| 2007/0102472 | A1 | 5/2007 | Shelton |
| 2007/0152014 | A1 | 7/2007 | Gillum et al. |
| 2007/0175949 | A1 | 8/2007 | Shelton et al. |
| 2007/0175950 | A1 | 8/2007 | Shelton et al. |
| 2007/0175951 | A1 | 8/2007 | Shelton et al. |
| 2007/0175955 | A1 | 8/2007 | Shelton et al. |
| 2007/0175961 | A1 | 8/2007 | Shelton et al. |
| 2008/0029570 | A1 | 2/2008 | Shelton et al. |
| 2008/0029573 | A1 | 2/2008 | Shelton et al. |
| 2008/0029574 | A1 | 2/2008 | Shelton et al. |
| 2008/0029575 | A1 | 2/2008 | Shelton et al. |
| 2008/0058801 | A1 | 3/2008 | Taylor et al. |
| 2008/0109012 | A1 | 5/2008 | Falco et al. |
| 2008/0110958 | A1 | 5/2008 | McKenna et al. |
| 2008/0185419 | A1 | 8/2008 | Smith et al. |
| 2008/0208195 | A1 | 8/2008 | Shores et al. |
| 2008/0251561 | A1 | 10/2008 | Eades et al. |
| 2008/0255413 | A1 | 10/2008 | Zemlok et al. |
| 2008/0255607 | A1 | 10/2008 | Zemlok |
| 2008/0262654 | A1 | 10/2008 | Omori et al. |
| 2009/0090763 | A1 | 4/2009 | Zemlok et al. |
| 2009/0099876 | A1 | 4/2009 | Whitman |
| 2009/0138006 | A1 | 5/2009 | Bales et al. |
| 2009/0182193 | A1 | 7/2009 | Whitman et al. |
| 2009/0209990 | A1 | 8/2009 | Yates et al. |
| 2009/0254094 | A1 | 10/2009 | Knapp et al. |
| 2010/0225073 | A1 | 9/2010 | Porter et al. |
| 2011/0077673 | A1 | 3/2011 | Grubac et al. |
| 2011/0121049 | A1 | 5/2011 | Malinouskas et al. |
| 2011/0125138 | A1 | 5/2011 | Malinouskas et al. |
| 2011/0139851 | A1 | 6/2011 | McCuen |
| 2011/0155783 | A1 | 6/2011 | Rajappa et al. |
| 2011/0174099 | A1 | 7/2011 | Ross et al. |
| 2011/0204119 | A1 | 8/2011 | McCuen |
| 2011/0218522 | A1 | 9/2011 | Whitman |
| 2011/0253765 | A1 | 10/2011 | Nicholas et al. |
| 2011/0290854 | A1 | 12/2011 | Timm et al. |
| 2011/0295242 | A1 | 12/2011 | Spivey et al. |
| 2011/0295269 | A1 | 12/2011 | Swensgard et al. |
| 2012/0000962 | A1 | 1/2012 | Racenet et al. |
| 2012/0089131 | A1 | 4/2012 | Zemlok et al. |
| 2012/0143002 | A1 | 6/2012 | Aranyi et al. |
| 2012/0223121 | A1 | 9/2012 | Viola et al. |
| 2012/0253329 | A1 | 10/2012 | Zemlok et al. |
| 2012/0310220 | A1 | 12/2012 | Malkowski et al. |
| 2012/0323226 | A1 | 12/2012 | Chowaniec et al. |
| 2013/0018361 | A1 | 1/2013 | Bryant |
| 2013/0098966 | A1 | 4/2013 | Kostrzewski et al. |
| 2013/0098968 | A1 | 4/2013 | Aranyi et al. |
| 2013/0098969 | A1 | 4/2013 | Scirica et al. |
| 2013/0214025 | A1 | 8/2013 | Zemlok et al. |
| 2013/0240596 | A1 | 9/2013 | Whitman |
| 2013/0274722 | A1 | 10/2013 | Kostrzewski et al. |
| 2013/0282052 | A1 | 10/2013 | Aranyi et al. |
| 2013/0319706 | A1 | 12/2013 | Nicholas et al. |
| 2013/0324978 | A1 | 12/2013 | Nicholas et al. |
| 2013/0324979 | A1 | 12/2013 | Nicholas et al. |
| 2013/0334281 | A1 | 12/2013 | Williams |
| 2014/0012236 | A1 | 1/2014 | Williams et al. |
| 2014/0012237 | A1 | 1/2014 | Pribanic et al. |
| 2014/0012289 | A1 | 1/2014 | Snow et al. |
| 2014/0025046 | A1 | 1/2014 | Williams et al. |

FOREIGN PATENT DOCUMENTS

| | | | |
|---|---|---|---|
| DE | 102008053842 | A1 | 5/2010 |
| EP | 0634144 | A1 | 1/1995 |
| EP | 0648476 | A1 | 4/1995 |
| EP | 0686374 | A2 | 12/1995 |
| EP | 1690502 | A1 | 8/2006 |
| EP | 1736112 | A1 | 12/2006 |
| EP | 1769754 | A1 | 4/2007 |
| EP | 1 813 203 | A2 | 8/2007 |
| EP | 1813199 | A1 | 8/2007 |
| EP | 1813211 | A2 | 8/2007 |
| EP | 1943958 | A1 | 7/2008 |
| EP | 1943976 | A2 | 7/2008 |
| EP | 2005898 | A2 | 12/2008 |
| EP | 2027819 | A1 | 2/2009 |
| EP | 2055243 | A2 | 5/2009 |
| EP | 2098170 | A2 | 9/2009 |
| EP | 2100561 | A2 | 9/2009 |
| EP | 2165664 | A2 | 3/2010 |
| EP | 2236098 | A2 | 10/2010 |
| EP | 2263568 | A2 | 12/2010 |
| EP | 2329773 | A1 | 6/2011 |
| EP | 2333509 | A1 | 6/2011 |
| EP | 2462880 | A2 | 6/2012 |
| EP | 2491872 | A1 | 8/2012 |
| EP | 2586382 | A2 | 5/2013 |
| EP | 2606834 | A2 | 6/2013 |
| EP | 2676615 | A2 | 12/2013 |
| WO | 00/72760 | A1 | 12/2000 |
| WO | 00/72765 | A1 | 12/2000 |
| WO | 03/000138 | A2 | 1/2003 |
| WO | 03/026511 | A1 | 4/2003 |
| WO | 03/077769 | A1 | 9/2003 |
| WO | 2004/107989 | A1 | 12/2004 |
| WO | 2006/042210 | A2 | 4/2006 |
| WO | 2007/026354 | A1 | 3/2007 |
| WO | 2008/131362 | A2 | 10/2008 |
| WO | 2008/133956 | A2 | 11/2008 |
| WO | 2009039506 | A1 | 3/2009 |
| WO | 2007014355 | A3 | 4/2009 |
| WO | 2009/132359 | A2 | 10/2009 |
| WO | 2011/108840 | A2 | 9/2011 |

OTHER PUBLICATIONS

Extended European Search Report corresponding to EP 08 25 2703.7, completed Oct. 23, 2008 and mailed Oct. 31, 2008; (7 pp.).

Extended European Search Report corresponding to EP 08 25 3184.9, completed Feb. 12, 2009 and mailed Feb. 27, 2009; (3 pp.).

Extended European Search Report corresponding to EP 10 25 0228.3, completed May 20, 2010 and mailed Jun. 1, 2010; (6 pp.).

Extended European Search Report corresponding to EP 10 25 2037.6, completed Mar. 1, 2011 and mailed Mar. 9, 2011; (3 pp.).

Extended European Search Report corresponding to EP 10 25 1968.3, completed on Jul. 4, 2011 and mailed Jul. 14, 2011; (12 pp.).

Extended European Search Report corresponding to EP 11 15 2266.0, completed Jul. 15, 2011 and mailed Jul. 28, 2011; (3 pp.).

Extended European Search Report corresponding to EP 11 25 0462.6, completed Jul. 20, 2011 and mailed Jul. 28, 2011; (6 pp.).

Extended European Search Report corresponding to EP 11 25 0771.0, completed Feb. 7, 2012 and mailed Feb. 17, 2012; (3 pp.).

Extended European Search Report corresponding to EP 06 78 8914.7, completed May 3, 2012 and mailed May 11, 2012; (8 pp.).

Partial European Search Report corresponding to EP 12 18 6177.7, completed Jan. 30, 2013 and mailed Feb. 12, 2013; (6 pp.).

Extended European Search Report corresponding to EP No. 11 17 8021.9, mailed Jun. 4, 2013; (3 pp).

Extended European Search Report corresponding to EP No. 13 16 3033.7, completed Jun. 27, 2013 and mailed Jul. 15, 2013; (8 pp).

Extended European Search Report corresponding to EP No. 12 18 6177.7, completed Aug. 14, 2013 and mailed Aug. 23, 2013; (8 pp).

Partial European Search Report corresponding to EP No. 13 17 1742.3, completed Sep. 17, 2013 and mailed Sep. 25, 2013; (8 pp).

Partial European Search Report corresponding to EP No. 13 17 2400.7, completed Sep. 18, 2013 and mailed Oct. 1, 2013; (7 pp).

Extended European Search Report corresponding to EP No. 13 17 5475.6, completed Sep. 23, 2013 and mailed Oct. 1, 2013; (8 pp).

Extended European Search Report corresponding to EP No. 13 17 5478.0, completed Sep. 24, 2013 and mailed Oct. 2, 2013; (6 pp).

(56) References Cited

OTHER PUBLICATIONS

Extended European Search Report corresponding to EP No. 13 17 5479.8, completed Sep. 27, 2013 and mailed Oct. 10, 2013; (7 pp).
Partial Extended European Search Report corresponding to EP 13 17 5477.2, completed Oct. 7, 2013 and mailed Oct. 15, 2013; (7 pp).
Extended European Search Report corresponding to EP No. 08 25 2703.7, completed Oct. 23, 2008 and mailed Oct. 31, 2008; (7 pp).
European search Report from Appl. No. 13177163.6 dated Nov. 15, 2013. (8 pp).
Extended European Search Report from EP Application No. 13172400.7 dated Jan. 21, 2014.
Extended European Search Report from EP Application No. 13189026.1 dated Jan. 31, 2014.
The extended European Search Report from Application No. EP 13177163.6 dated Feb. 6, 2014.
Extended European Search Report from Application No. EP 13175477.2 dated Feb. 6, 2014.
Extended European Search Report from Application No. EP 13169998.5 dated Feb. 24, 2014.
Extended European Search Report corresponding to EP 13176805.3, dated Nov. 4, 2013.
Extended European Search Report from Application No. EP 13171742.3 dated Jan. 3, 2014.

* cited by examiner

APPARATUS FOR ENDOSCOPIC PROCEDURES

CROSS REFERENCE TO RELATED APPLICATIONS

This application is a continuation of U.S. patent application Ser. No. 13/444,228, filed on Apr. 11, 2012, now U.S. Pat. No. 8,672,206, which is a continuation-in-part of U.S. patent application Ser. No. 13/280,898 filed on Oct. 25, 2011 pending, and a continuation-in-part of application Ser. No. 13/280,859 filed on Oct. 25, 2011, now U.S. Pat. No. 8,657,177, the entire contents of all of which is incorporated by reference herein.

BACKGROUND

1. Technical Field

The present disclosure relates to surgical apparatuses, devices and/or systems for performing endoscopic surgical procedures and methods of use thereof. More specifically, the present disclosure relates to electromechanical, hand-held surgical apparatus, devices and/or systems configured for use with removable disposable loading units and/or single use loading units for clamping, cutting and/or stapling tissue.

2. Background of Related Art

A number of surgical device manufacturers have developed product lines with proprietary drive systems for operating and/or manipulating electromechanical surgical devices. In many instances the electromechanical surgical devices include a reusable handle assembly, and disposable or single use loading units. The loading units are selectively connected to the handle assembly prior to use and then disconnected from the handle assembly following use in order to be disposed of or in some instances sterilized for re-use.

Many of these electromechanical surgical devices are relatively expensive to manufacture, purchase and/or operate. There is a constant desire by manufactures and end users to develop electromechanical surgical devices that are relatively inexpensive to manufacture, purchase and/or operate. A need exists for electromechanical surgical apparatus, devices and/or systems having improved mechanical linkages.

SUMMARY

Further details and aspects of exemplary embodiments of the present invention are described in more detail below with reference to the appended Figures.

In one aspect of the present disclosure, a surgical system comprises a handle assembly including a housing, and a jaw assembly including: a removable cartridge assembly including a plurality of fasteners and a longitudinal slot defined therein; an anvil having a fastener forming surface thereon, the cartridge assembly and anvil being mounted for movement with respect to one another between an open position and a closed position in close cooperative alignment for clamping tissue; an actuation sled supported within the cartridge assembly, the actuation sled being movable to urge the plurality of fasteners from the cartridge; a drive beam including a vertical support strut and a cam member supported on the vertical support strut, the cam member being positioned to translate relative to the anvil to maintain the anvil in the closed position during firing of the fasteners and the vertical support strut being positioned to abut the actuation sled; and a drive screw supported within the removable cartridge assembly, the drive screw having a threaded portion, wherein the drive beam is threadably coupled to the threaded portion of the drive screw such that rotation of the drive screw imparts longitudinal movement of the drive beam. The surgical system also includes an elongated body configured to interconnect the handle assembly and the jaw assembly, the elongated body including a flexible drive shaft mechanically coupling the drive screw to an actuation shaft of the handle assembly, wherein the drive shaft transfers rotational motion of the actuation shaft to the drive screw, the elongated body including a flexible portion, and wherein the flexible drive shaft is housed within the flexible portion.

In certain embodiments, the surgical system flexible portion includes a plurality of interlocking segments. A drive link may interconnect the flexible drive shaft and the drive screw. The drive screw may define a first longitudinal axis and the flexible drive shaft defines a second longitudinal axis, and the drive link may be disposed off-axis in relation to the first and second longitudinal axes.

In certain embodiments, the drive link includes a proximal engagement portion mechanically coupled to the flexible drive shaft and a distal engagement portion mechanically coupled to the drive screw. The proximal engagement portion may include a socket configured and dimensioned to mechanically interface with a ball joint disposed at a distal end of the flexible drive shaft. The distal engagement portion may include a pin configured and dimensioned to mechanically interface with a clevis disposed at a proximal end of the drive screw.

In certain embodiments, the surgical system has a surgical buttress releasably secured to a tissue contacting surface of at least one of the anvil or the staple cartridge, wherein the surgical buttress is secured to the at least one of the anvil assembly and the cartridge assembly by at least one anchor, and wherein at least one of the anvil assembly and the cartridge assembly define a side slot for receiving an end of the at least one anchor therein, and a release assembly disposed within at least one of the anvil assembly or the cartridge assembly.

The drive screw can be configured to actuate the release assembly to thereby release the anchor and to free the surgical buttress from the at least one of the anvil assembly and cartridge assembly. The release assembly may further include a first bar extending across the longitudinal slot prior to an actuation of the drive assembly, and a second bar operatively connected to and actuatable by the first bar, the second bar having an end extending at least partially into the side slot, prior to an actuation of the drive assembly.

In a further aspect of the present disclosure, a surgical system comprises a handle assembly including a housing, a jaw assembly adjacent a distal end of the elongated body, the jaw assembly including: a cartridge assembly including a plurality of fasteners and a longitudinal slot defined therein; an anvil having a fastener forming surface thereon, the cartridge assembly and anvil being mounted for movement with respect to one another between an open position and a closed position in close cooperative alignment for clamping tissue; an actuation sled supported within the cartridge assembly, the actuation sled being movable to urge the plurality of fasteners from the cartridge; a drive beam including a vertical support strut and a cam member supported on the vertical support strut, the cam member being positioned to translate relative to the anvil to maintain the anvil in the closed position during firing of the fasteners and the vertical support strut being positioned to abut the actuation sled; and a drive screw defining a first longitudinal axis supported within the cartridge assembly, the drive screw having a threaded portion, wherein the drive beam is threadably coupled to the threaded portion of the drive screw such that rotation of the drive screw imparts longitudinal movement of the drive beam. The instrument also has an elongated body configured to interconnect the handle assembly and the jaw assembly, the elongated body including a flexible drive shaft mechanically coupling the drive screw to an actuation shaft of the handle assembly, wherein the drive shaft transfers rotational motion of the actuation shaft to the drive screw. A drive link interconnects the flexible drive shaft and the drive screw, the drive link being disposed off-axis in relation to the first and second longitudinal axes.

The surgical system elongated body may include a flexible portion housing the flexible drive shaft. The flexible portion may include a plurality of interlocking segments. The drive link may include a proximal engagement portion mechanically coupled to the flexible drive shaft and a distal engagement portion mechanically coupled to the drive screw. The proximal engagement portion can include a socket configured and dimensioned to mechanically interface with a ball joint disposed at a distal end of the flexible drive shaft. The distal engagement portion may include a pin configured and dimensioned to mechanically interface with a clevis disposed at a proximal end of the drive screw.

In certain embodiments, a surgical buttress is releasably secured to a tissue contacting surface of at least one of the anvil or the staple cartridge, wherein the surgical buttress is secured to the at least one of the anvil assembly and the cartridge assembly by at least one anchor, and wherein at least one of the anvil assembly and the cartridge assembly define a side slot for receiving an end of the at least one anchor therein. A release assembly is disposed within at least one of the anvil assembly or the cartridge assembly.

The drive screw may be configured to actuate the release assembly to thereby release the anchor and to free the surgical buttress from the at least one of the anvil assembly and cartridge assembly. The release assembly further includes a first bar extending across the longitudinal slot prior to an actuation of the drive assembly, and a second bar operatively connected to and actuatable by the first bar, the second bar having an end extending at least partially into the side slot, prior to an actuation of the drive assembly.

The surgical system handle assembly, the jaw assembly, and the elongated shaft assembly may be separable from each other.

In certain embodiments, the system includes: a power source is configured to provide electrical energy; a control assembly configured to accept at least one user input; a first motor coupled to the power source and configured to operate in response to the at least one user input; a second motor coupled to the power source and configured to operate in response to the at least one user input; and a selector gearbox assembly comprising at least one gear element mechanically coupled to the flexible drive shaft, wherein the first motor is configured to selectively move the at least one gear element into engagement with the second motor to actuate the flexible drive shaft.

In another aspect of the present disclosure, a surgical system comprises a handle assembly including a housing; a jaw assembly adjacent a distal end of the elongated body, the jaw assembly including: a cartridge assembly including a plurality of fasteners and a longitudinal slot defined therein; an anvil having a fastener forming surface thereon, the cartridge assembly and anvil being mounted for movement with respect to one another between an open position and a closed position in close cooperative alignment for clamping tissue; an actuation sled supported within the cartridge assembly, the actuation sled being movable to urge the plurality of fasteners from the cartridge; a drive beam including a vertical support strut and a cam member supported on the vertical support strut, the cam member being positioned to translate relative to the anvil to maintain the anvil in the closed position during firing of the fasteners and the vertical support strut being positioned to abut the actuation sled; and a drive screw defining a first longitudinal axis supported within the cartridge assembly, the drive screw having a threaded portion, wherein the drive beam is threadably coupled to the threaded portion of the drive screw such that rotation of the drive screw imparts longitudinal movement of the drive beam. The system has an elongated body configured to interconnect the handle assembly and the jaw assembly, the elongated body including a flexible drive shaft mechanically coupling the drive screw to an actuation shaft of the handle assembly, wherein the drive shaft transfers rotational motion of the actuation shaft to the drive screw, and a drive link interconnecting the flexible drive shaft and the drive screw, the drive link being disposed off-axis in relation to the first and second longitudinal axes. The handle assembly, the jaw assembly, and the elongated shaft assembly are separable from each other. The system includes: a power source configured to provide electrical energy; a control assembly configured to accept at least one user input; a first motor coupled to the power source and configured to operate in response to the at least one user input; a second motor coupled to the power source and configured to operate in response to the at least one user input; and a selector gearbox assembly comprising at least one gear element mechanically coupled to the flexible drive shaft, wherein the first motor is configured to selectively move the at least one gear element into engagement with the second motor to actuate the flexible drive shaft.

In a further aspect, a surgical system comprises a jaw assembly including: a cartridge assembly including a plurality of fasteners and a longitudinal slot defined therein; an anvil having a fastener forming surface thereon, the cartridge assembly and anvil being mounted for movement with respect to one another between an open position and a closed position in close cooperative alignment for clamping tissue; an actuation sled supported within the cartridge assembly, the actuation sled being movable to urge the plurality of fasteners from the cartridge; a drive beam including a cam member positioned to translate relative to the anvil to maintain the anvil in the closed position during firing of the fasteners; and a drive screw defining a first longitudinal axis supported within the cartridge assembly, the drive screw having a threaded portion, wherein the drive beam is threadably coupled to the threaded portion of the drive screw such that rotation of the drive screw imparts longitudinal movement of the drive beam. The instrument includes an elongated body configured to connect with the jaw assembly, the elongated body including a flexible drive shaft, the drive shaft transferring rotational motion to the drive screw, and a drive link interconnecting the flexible drive shaft and the drive screw, wherein the drive link is disposed off-axis in relation to the first and second longitudinal axes. The jaw assembly and the elongated shaft assembly are separable from each other, the elongated body being configured to connect with an actuator.

The surgical system, in certain embodiments, includes an actuator disposed in a handle assembly. A power source configured to provide electrical energy can be included. The system may include a control assembly configured to accept at least one user input.

In certain embodiments, the system has a first motor coupled to the power source and configured to operate in response to the at least one user input. A second motor may be coupled to the power source and configured to operate in response to the at least one user input. The system may have a selector gearbox assembly comprising at least one gear element mechanically coupled to the flexible drive shaft, the first motor being configured to selectively move the at least one gear element into engagement with the second motor to actuate the flexible drive shaft.

In certain embodiments, the drive beam includes a vertical support strut for supporting the cam member and pushing the sled. The system may have a housing having a motor therein. A control assembly configured to accept a user input can be included.

BRIEF DESCRIPTION OF THE DRAWINGS

Embodiments of the present disclosure are described herein with reference to the accompanying drawings, wherein.

DETAILED DESCRIPTION OF EMBODIMENTS

Figure 1:
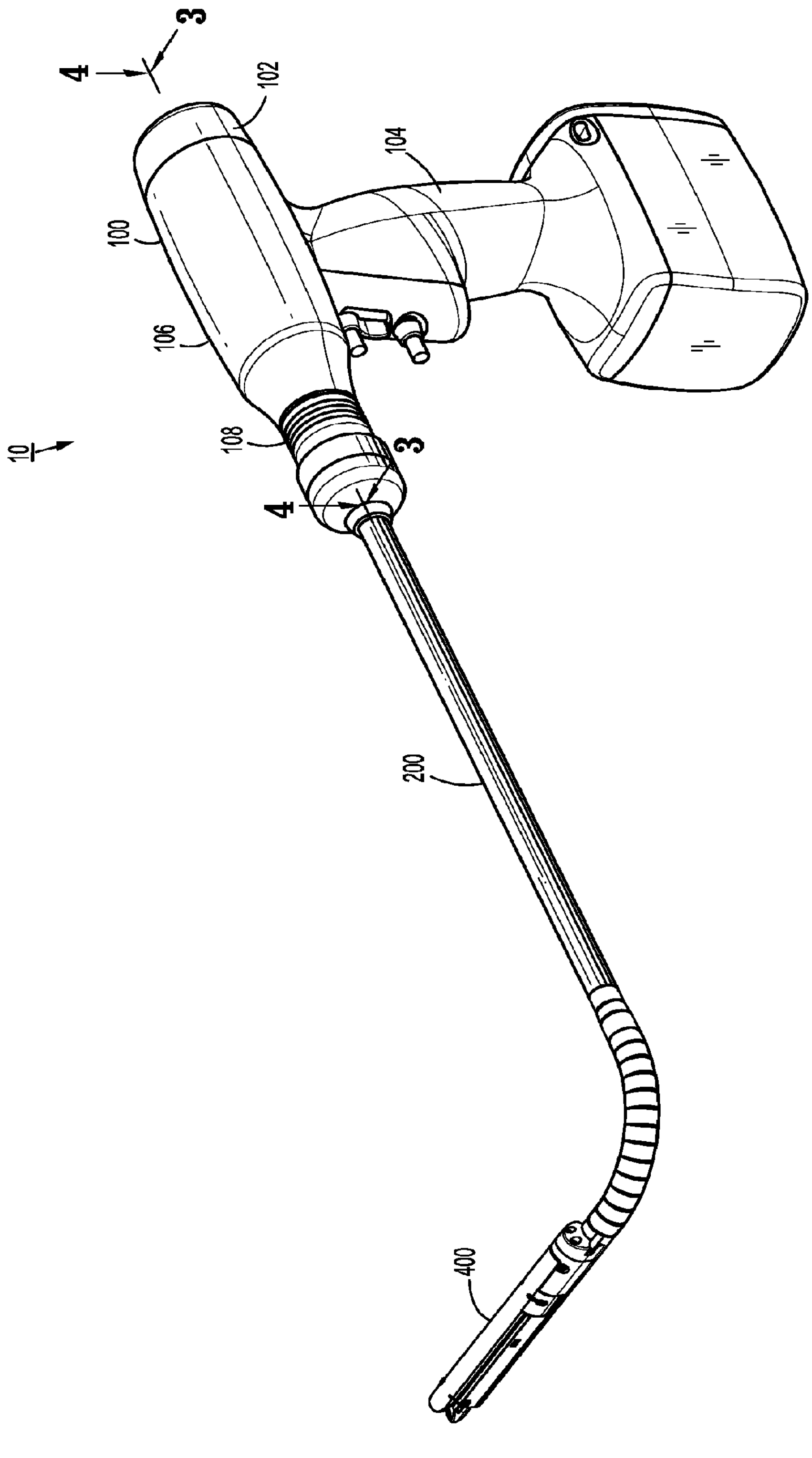
FIG. 1 is a perspective view of an electromechanical surgical system according to the present disclosure.
Figure 2:
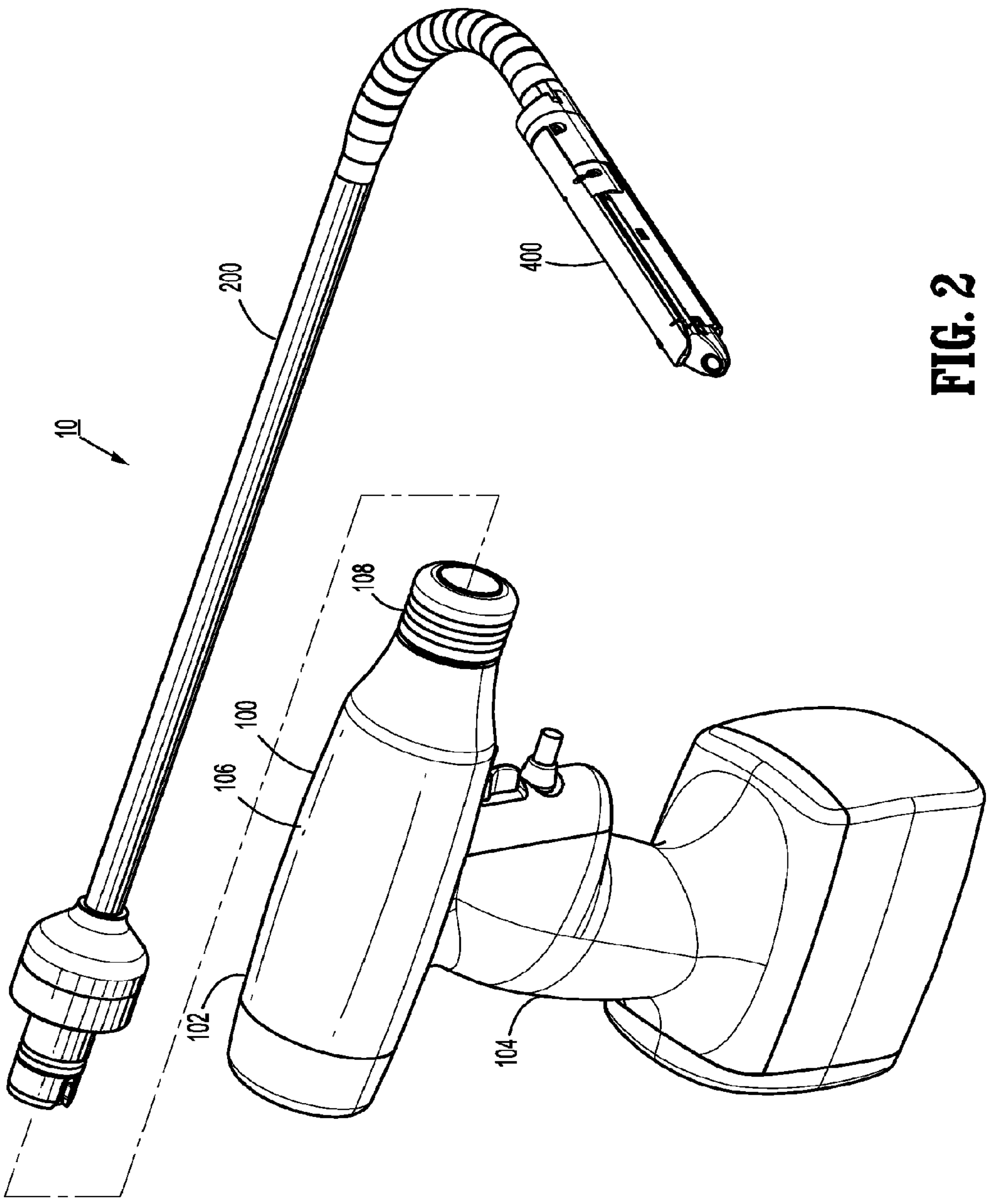
FIG. 2 is a disassembled, perspective view of a surgical instrument, an elongated member, and an end effector of the electrosurgical surgical system of FIG. 1, according to the present disclosure.

Embodiments of the presently disclosed electromechanical surgical system, apparatus and/or device are described in detail with reference to the drawings, in which like reference numerals designate identical or corresponding elements in each of the several views. As used herein the term “distal” refers to that portion of the electromechanical surgical system, apparatus and/or device, or component thereof, that are farther from the user, while the term “proximal” refers to that portion of the electromechanical surgical system, apparatus and/or device, or component thereof, that are closer to the user. The terms “left” and “right” refer to that portion of the electromechanical surgical system, apparatus and/or device, or component thereof, that are on the left (e.g., port) and right (e.g., starboard) sides, respectively, from the perspective of the user facing the distal end of the electromechanical surgical system, apparatus and/or device from the proximal end while the surgical system, apparatus and/or device is oriented in non-rotational configuration.

Referring initially to FIGS. 1-5, an electromechanical, hand-held, powered surgical system, in accordance with an embodiment of the present disclosure is shown and generally designated 10. Electromechanical surgical system 10 includes a surgical apparatus or device in the form of an electromechanical, hand-held, powered surgical instrument 100 that is configured for selective attachment thereto of a plurality of different end effectors 400, via a shaft assembly 200. The end effector 400 and the shaft assembly 200 are configured for actuation and manipulation by the electromechanical, hand-held, powered surgical instrument or handle assembly 100. In particular, the surgical instrument 100, the shaft assembly 200, and the end effector 400 are separable from each other such that the surgical instrument 100 is configured for selective connection with shaft assembly 200, and, in turn, shaft assembly 200 is configured for selective connection with any one of a plurality of different end effectors 400.

Reference may be made to International Application No. PCT/US2008/077249, filed Sep. 22, 2008 (Inter. Pub. No. WO 2009/039506) and U.S. patent application Ser. No. 12/622,827, filed on Nov. 20, 2009, the entire content of each of which is incorporated herein by reference, for a detailed description of the construction and operation of exemplary electromechanical, hand-held, powered surgical instrument 100.

Figure 3:
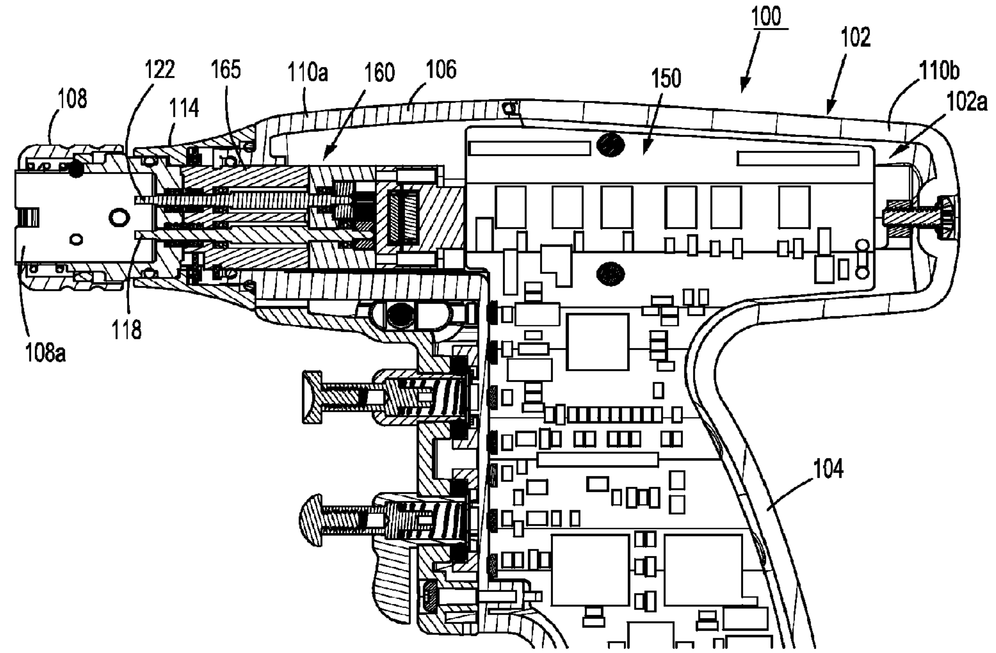
FIG. 3 is a side, cross-sectional view of the surgical instrument of FIG. 1, as taken through 3-3 of FIG. 1, according to the present disclosure.
Figure 4:
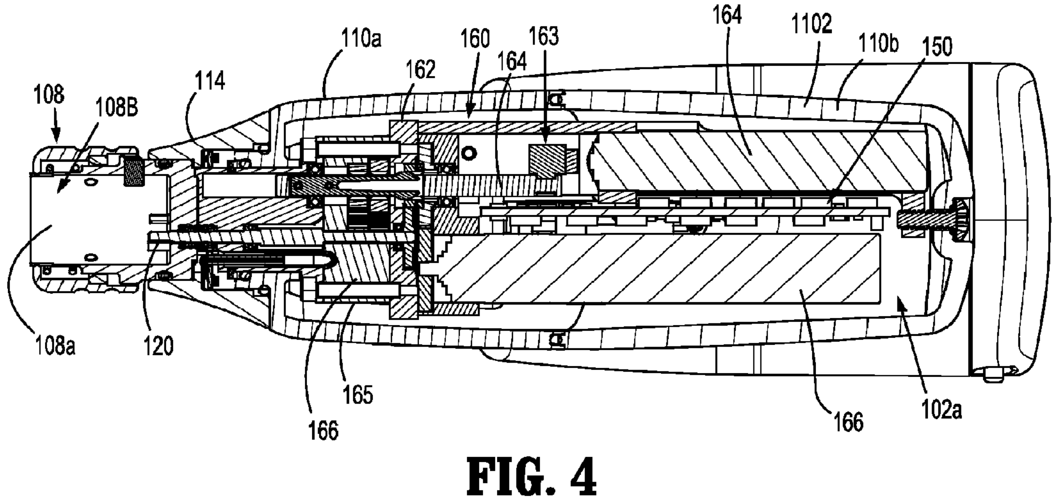
FIG. 4 is a top, cross-sectional view of the surgical instrument of FIG. 1, as taken through 4-4 of FIG. 1, according to the present disclosure.

Generally, as illustrated in FIGS. 1-4, surgical instrument or handle assembly 100 includes a handle housing 102 having a lower housing portion 104, an intermediate housing portion 106 extending from and/or supported on lower housing portion 104, and an upper housing portion 108 extending from and/or supported on intermediate housing portion 106. Intermediate housing portion 106 and upper housing portion 108 are separated into a distal half-section 110*a* that is integrally formed with and extending from the lower portion 104, and a proximal half-section 110*b* connectable to distal half-section 110*a* by a plurality of fasteners (FIGS. 3 and 4). When joined, distal and proximal half-sections 110*a*, 110*b* define the handle housing 102 having a cavity 102*a* therein in which a control assembly 150 and a drive mechanism 160 are disposed. The instrument 100 also includes a power source (not shown), which is coupled to the control assembly 150 and the drive mechanism 160. Control assembly 150 may include one or more logic controllers and/or user interfaces (e.g., switches, buttons, triggers, touch screens, etc.) and is configured to control the various operations of the instrument 100, in particular, the drive mechanism 160, as discussed in further detail below. The handle assembly may be configured to be grasped by a user of the surgical system, or may be configured as a console connectable to the shaft assembly or elongated body discussed below.

Lower housing portion 104 of the instrument 100 defines an aperture (not shown) formed in an upper surface thereof and which is located beneath or within intermediate housing portion 106. The aperture of lower housing portion 104 provides a passage through which wires and other various electrical leads interconnect electrical components (e.g., power source and any corresponding power control circuitry) situated in lower housing portion 104 with electrical components (e.g., control assembly 150, drive mechanism 160, etc.) situated in intermediate housing portion 106 and/or upper housing portion 108.

With reference to FIGS. 3 and 4, distal half-section 110*a* of upper housing portion 108 defines a nose or connecting portion 108*a*. A nose cone 114 is supported on nose portion 108*a* of upper housing portion 108. Upper housing portion 108 of handle housing 102 provides a housing in which drive mechanism 160 is disposed. The drive mechanism 160 is configured to drive shafts and/or gear components in order to perform the various operations of instrument 100. In particular, drive mechanism 160 is configured to drive shafts and/or gear components in order to selectively rotate the end effector 400 about a longitudinal axis A-A (FIGS. 6A and 6B) relative to handle housing 102, to move jaw members of the end effector 400 relative to each other, and/or to fire the fasteners, to cut the tissue grasped within the end effector 400.

Figure 5:
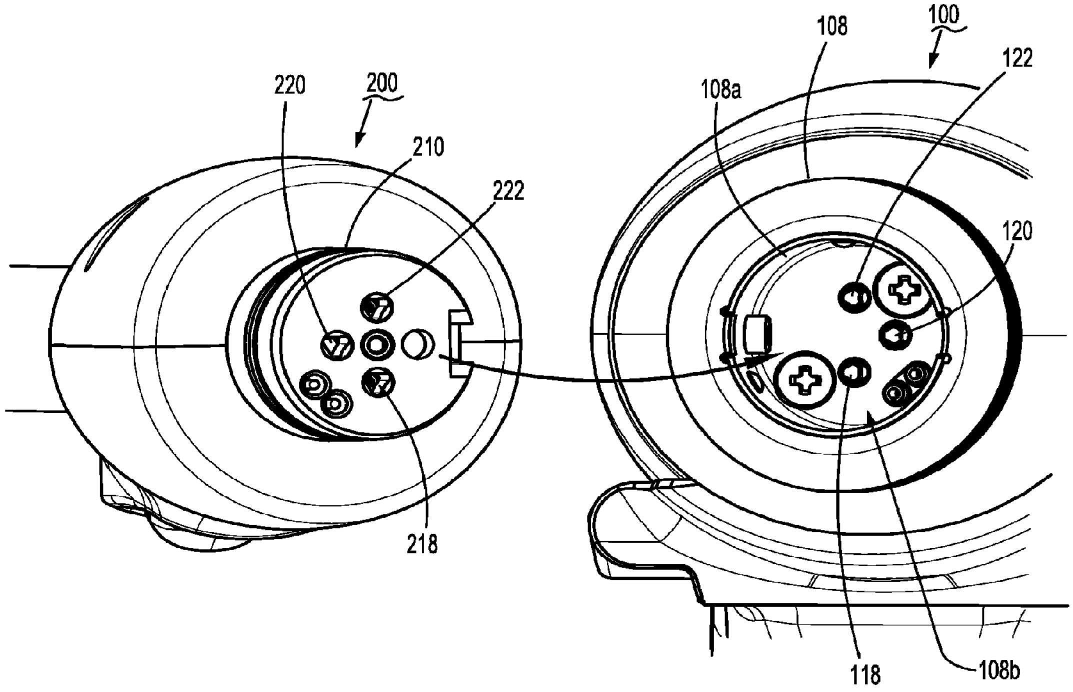
FIG. 5 is a front, perspective view of the surgical instrument of FIG. 1 with the elongated member of FIG. 2 separated therefrom, according to the present disclosure.

As seen in FIGS. 3 and 4, drive mechanism 160 includes a selector gearbox assembly 162 that is located immediately proximal relative to a shaft assembly 200. Proximal to the selector gearbox assembly 162 is a function selection module 163 having a first motor 164 that functions to selectively move gear elements within the selector gearbox assembly 162 into engagement with an input drive component 165 having a second motor 166. With particular reference to FIG. 5, the distal half-section 110*a* of upper housing portion 108 defines a connecting portion 108*a* configured to accept a corresponding drive coupling assembly 210 of the shaft assembly 200.

With continued reference to FIG. 5, the connecting portion 108*a* of instrument 100 includes a cylindrical recess 108*b* that receives a drive coupling assembly 210 of shaft assembly 200. Connecting portion 108*a* houses three rotatable drive connectors 118, 120, 122. When shaft assembly 200 is mated to instrument 100, each of rotatable drive connectors, namely, first drive connector 118, second drive connector 120, and third drive connector 122 of instrument 100, mechanically engage a corresponding rotatable connector sleeve, namely, first connector sleeve 218, second connector sleeve 220, and third connector sleeve 222 of shaft assembly 200.

The mating of drive connectors 118, 120, 222 of instrument 100 with connector sleeves 218, 220, 222 of shaft assembly 200 allows rotational forces to be independently transmitted via each of the three respective connector interfaces. The drive connectors 118, 120, 122 of instrument 100 are configured to be independently rotated by drive mechanism 160. In this regard, the function selection module 163 of drive mechanism 160 selects which drive connector or connectors 118, 120, 122 of instrument 100 is to be driven by the input drive component 165 of drive mechanism 160.

With continued reference to FIGS. 3 and 4, drive mechanism 160 includes a selector gearbox assembly 162 and a function selection module 163, located proximal to the selector gearbox assembly 162 that functions to selectively move gear elements within the selector gearbox assembly 162 into engagement with second motor 166. Thus, drive mechanism 160 selectively drives one or more of drive connectors 118, 120, 122 of instrument 100 at a given time.

Since each of drive connectors 118, 120, 122 of instrument 100 has a keyed and/or substantially non-rotatable interface with respective connector sleeves 218, 220, 222 of shaft assembly 200, when shaft assembly 200 is coupled to instrument 100, rotational force(s) are selectively transferred from drive mechanism 160 of instrument 100 to shaft assembly 200.

The selective rotation of drive connector(s) 118, 120 and/or 122 of instrument 100 allows instrument 100 to selectively actuate different functions of the end effector 400. In embodiments, any number of the drive connectors 118, 120, and/or 122 may be used to operate the end effector 400. As will be discussed in greater detail below, selective and independent rotation of first drive connector 118 of instrument 100 corresponds to the selective and independent opening and closing of the jaw members of the end effector 400, and driving of the actuation sled 440 (FIG. 8) of end effector 400. The selective and independent rotation of the third drive connectors 120, 122 of instrument 100 corresponds to the selective and independent pivoting of the camera assembly 500 rotation relative to the end effector 400. The drive connector 120 may be used to pivot and/or rotate the end effector 400 relative to the shaft assembly 200.

Figure 6:
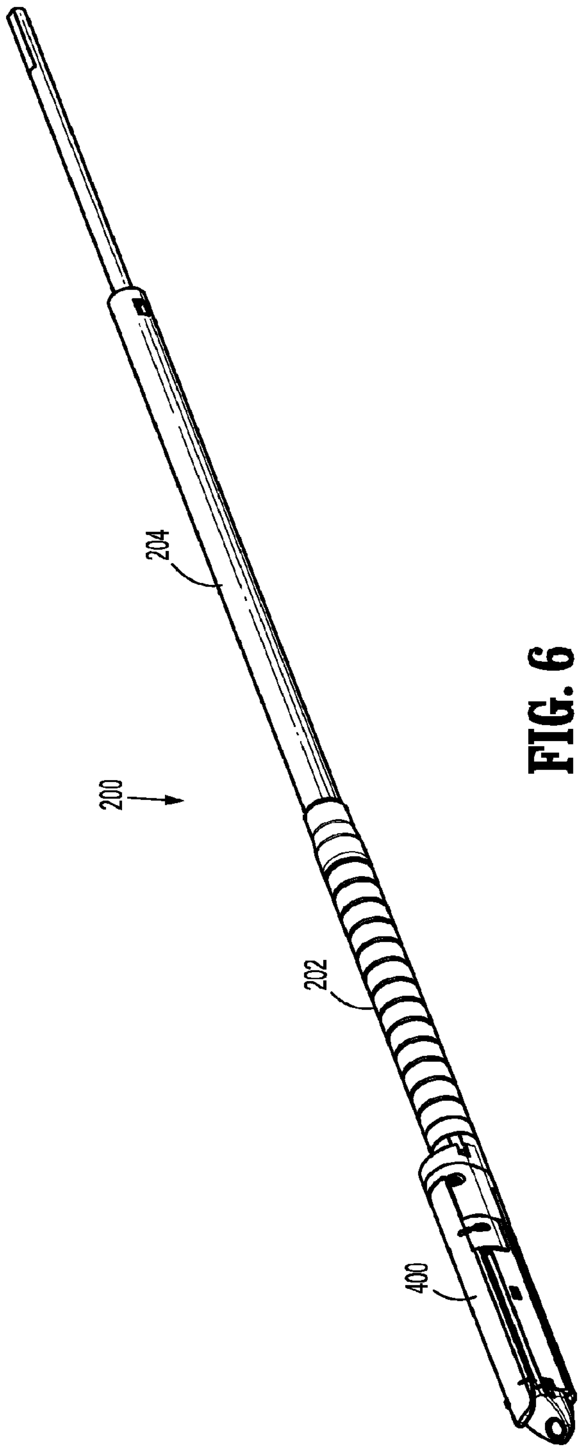
FIG. 6 is a front, perspective view of the end effector of FIG. 1, according to the present disclosure.
Figure 7:
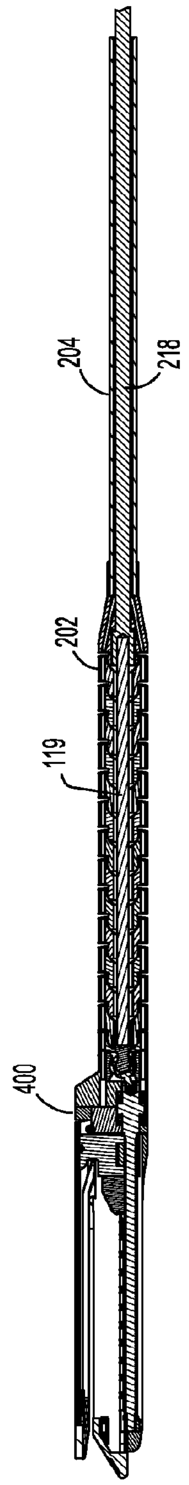
FIG. 7 is a side, cross-sectional view of the end effector of FIG. 1, according to the present disclosure.
Figure 8:
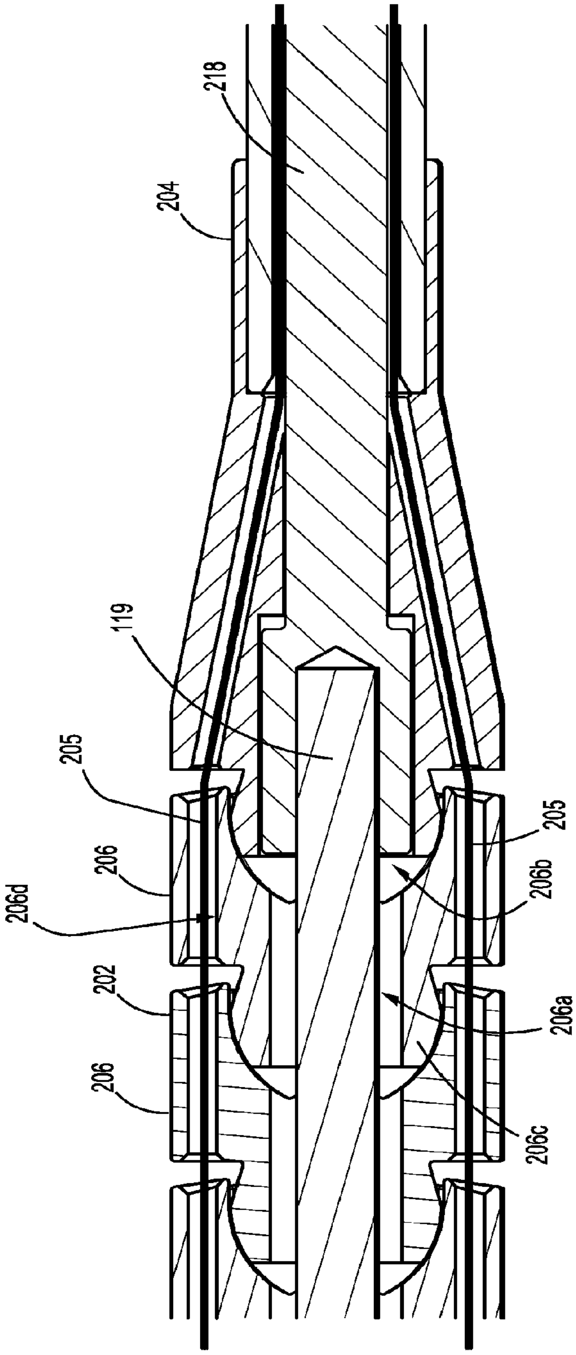
FIG. 8 is an enlarged, side, cross-sectional view of the end effector of FIG. 1, according to the present disclosure.

FIG. 6 shows the elongated body or shaft assembly 200 and the end effector 400. The elongated body or shaft assembly 200 includes a flexible portion 202 interconnecting a rigid portion 204 and the end effector 400. As shown in FIGS. 7 and 8, the rigid portion 204 houses the first connector sleeve 218, which is coupled to a flexible drive shaft 119 extending through flexible portion 202. The shaft 119 may be formed from any suitable flexible and torsionally stiff material that may be articulated along with the flexible portion 202 to allow for the articulation of the end effector 400 relative to the rigid portion 204 between a non-articulated position in which a first longitudinal axis defined by the end effector 400 is substantially aligned with a second longitudinal axis defined by the rigid portion 204; and an articulated position in which the longitudinal axis of end effector 400 is disposed at a substantially non-zero angle relative to the second longitudinal axis of the rigid portion 204. Shaft 119 may be fabricated from stainless steel or the like.

As seen in FIG. 8, the flexible portion 202 includes a plurality of interlocking segments 206 each defining an opening **206*a* therethrough. The shaft 119 is disposed within the openings 206*a* as shown in FIG. 8. Each of the interlocking segments 206 includes a socket 206*b* at its proximal end and a ball joint 206*c* at its distal end. The ball join 206*c* of one segment 206 is configured and dimensioned to interface with the socket 206*b* of the distal neighboring segment 206 allowing the entire flexible portion 202 to flex and thereby articulate in any desired direction through 360° around a longitudinal axis of rigid portion 204**.

Figure 9:
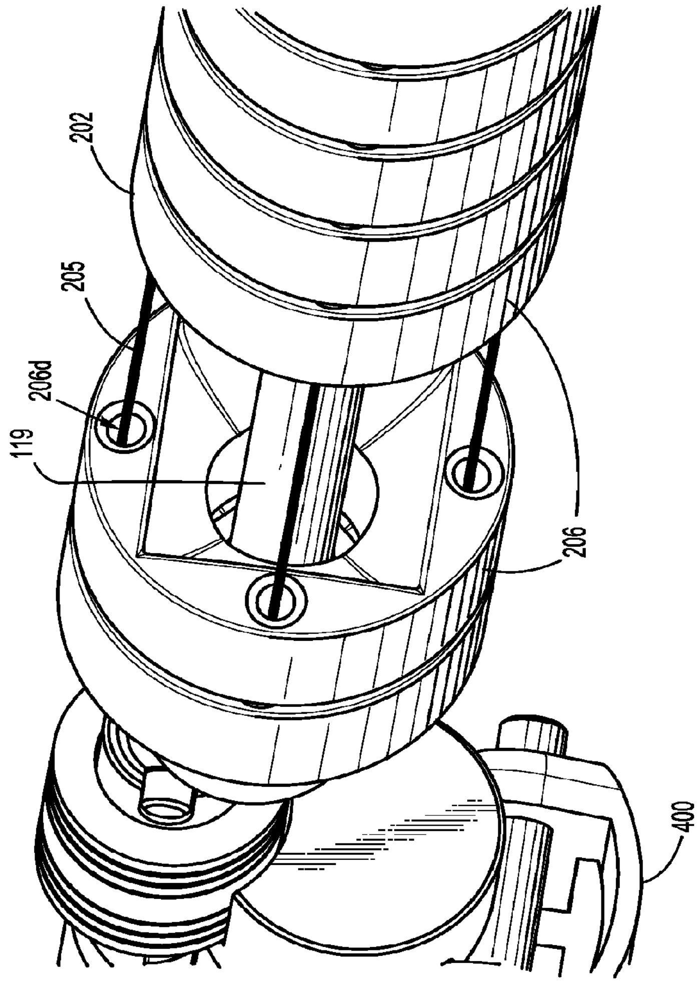
FIG. 9 is an enlarged, perspective, rear view of the end effector of FIG. 1, according to the present disclosure.

Articulation of the flexible portion 202 may be accomplished by tension cables 205. In embodiments, four equally radially-spaced apart cables may be used, which are coupled to the end effector 400 and passing them through the flexible portion 202. In particular, as shown in FIG. 9, each cable 205 may be disposed within a respective opening **206*d* of the segments 206. Thus, tension applied to one or more of cables would adjust direction of articulation of the flexible portion 202**. A cable articulation instrument is disclosed in a commonly-owned U.S. Provisional Patent Application No. 61/510,091, entitled "Articulating Links With Middle Link Control System", the entire contents of which are incorporated by reference herein.

FIGS. 10-14 illustrate components and operation of the end effector 400. End effector 400 has a jaw assembly, which includes a cartridge assembly 432 and an anvil 434. Cartridge assembly 432 houses one or more fasteners 433 (FIG. 10) that are disposed therewithin and is configured to deploy the fasteners 433 upon filing of instrument 100. The anvil 434 is movably (e.g., pivotally) mounted to the end effector 400 and is movable between an open position, spaced apart from cartridge assembly 432, and a closed position wherein anvil 434 is in close cooperative alignment with cartridge assembly 432, to thereby clamp tissue.

Figure 10:
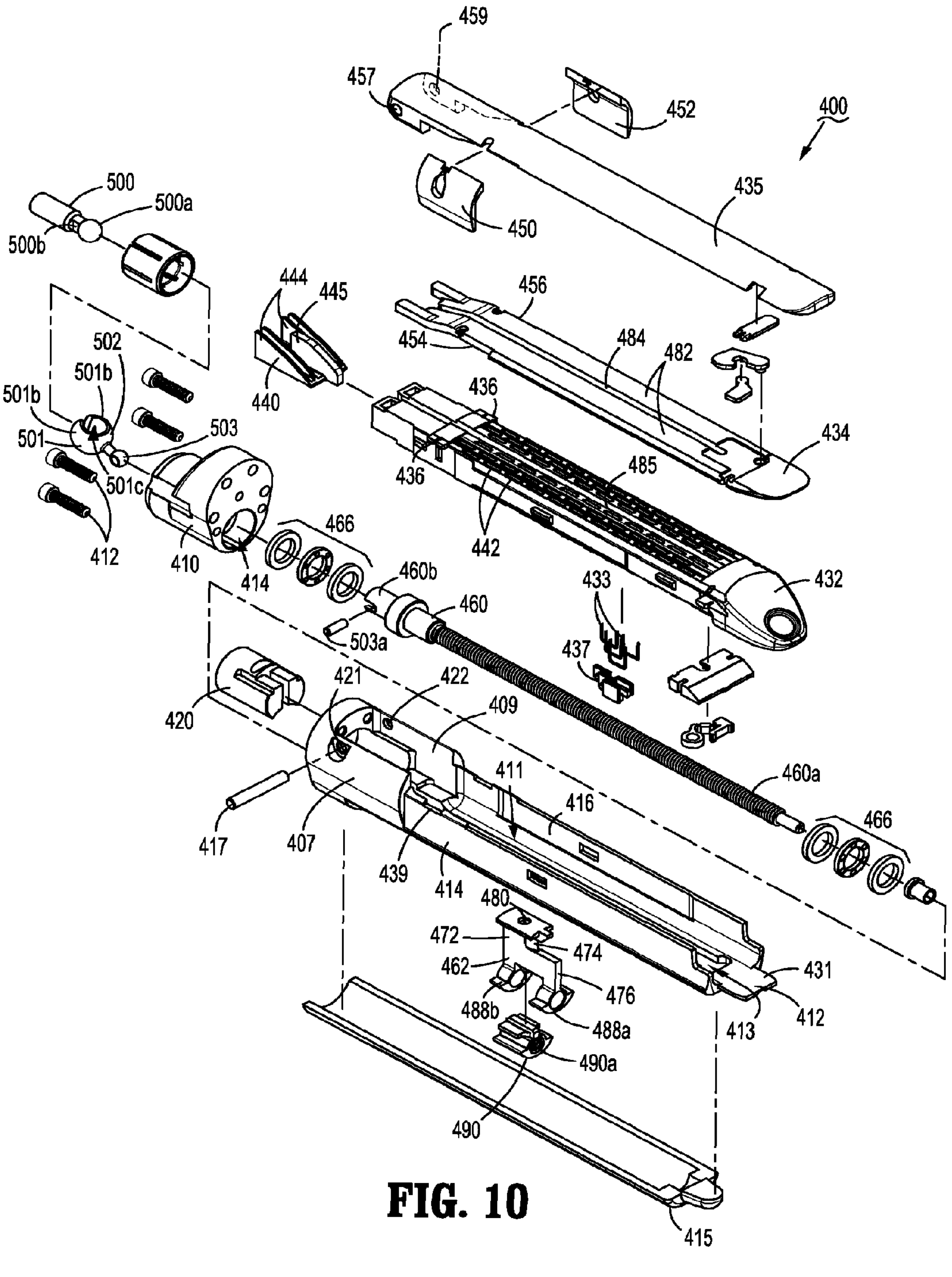
FIG. 10 is an exploded, perspective view of the end effector of FIG. 1, according to the present disclosure.

Referring to FIG. 10, an exploded view of the end effector 400 is shown. The end effector 400 also includes a carrier 431 having an elongate channel 411, a base 412 and two parallel upstanding walls 414 and 416 which include several mounting structures, such as notches 439, for supporting the cartridge assembly 432 and the anvil 434. A longitudinal slot 413 extends through the elongate channel 411.

The carrier 431 also includes a plate cover 415 disposed on a bottom surface thereof. The plate cover 415 is configured to frictionally engage with channel 411 of the carrier 431 and functions to protect tissue from moving parts along the exterior of carrier 431. The carrier 431 also includes a pair of tabs 407 and 409 disposed at a proximal end of respective walls 414, 416, and being configures for coupling to a housing portion 410 of end effector 400.

With continuing reference to FIG. 10, the distal portion of channel 411 supports the cartridge assembly 432 which contains the plurality of surgical fasteners 433 and a plurality of corresponding ejectors or pushers 437. End effector 400 includes an actuation sled 440 having upstanding cam wedges 444 configured to exert a fastener driving force on the pushers 437, which drive the fasteners 433 from cartridge assembly 432, as described in more detail below. Cartridge assembly 432 is maintained within channel 411 by lateral struts 436 which frictionally engage corresponding notches 439 formed in the upper surfaces of channel walls 414 and 416. These structures serve to restrict lateral, longitudinal, and elevational movement of the cartridge assembly 432 within channel 411.

A plurality of spaced apart longitudinal slots (not shown) extend through cartridge assembly 432 and accommodate the upstanding cam wedges 444 of actuation sled 440. The slots communicate with a plurality of pockets 442 within which the plurality of fasteners 433 and pushers 437 are respectively supported. The pushers 437 are secured by a pusher retainer (not shown) disposed below the cartridge assembly 432, which supports and aligns the pushers 437 prior to engagement thereof by the actuation sled 440. During operation, as actuation sled 440 translates through cartridge assembly 432, the angled leading edges of cam wedges 444 sequentially contact pushers 437 causing the pushers to translate vertically within slots 446, urging the fasteners 434 therefrom. The cartridge assembly 432 also includes a longitudinal slot 485 to allow for the knife blade 474 to travel therethrough, as described in more detail below.

With continuing reference to FIG. 10, the end effector 400 includes an anvil cover 435 disposed over the anvil 434. The anvil cover 435 protects tissue from moving parts along the exterior of anvil 434. The anvil cover 435 includes opposed mounting wings 450 and 452 which are dimensioned and configured to engage detents 454 and 456 of the anvil 434, respectively. The mounting wings 450 and 452 function to align the anvil 434 with the cartridge assembly 432 during closure. The anvil 434 and the cover 435 are configured to remain in an open configuration until closed, as described in more detail below.

The anvil 434 is pivotally coupled to the carrier 431. The carrier 431 includes a pair of openings 421 and 422 formed in respective tabs 407, 409. The anvil cover 435 also includes a pair of opposed openings 457 and 459 found therein. A pivot pin 417, or a pair of pins, passes through the openings 421, 422, 457, and 459 allowing for pivotal coupling of the anvil 434 to the carrier 431.

As seen in FIG. 10, end effector 400 further includes an axial drive screw 460 for transmitting the rotational drive forces exerted by the flexible drive shaft 119 to actuation sled 440 during a stapling procedure. Drive screw 460 is rotatably supported in carrier 431 and includes a threaded portion 460*a* and a proximal engagement portion 460*b*. The drive screw 460 is rotatably secured at a distal end of the cartridge 432 and includes one or more bearings 466 frictionally fitted about the engagement portion 460*b*. This allows the drive screw 460 to be rotated relative to the carrier 431. Distal housing member 410 of the effector 400 is coupled to the proximal end of the carrier 431 via one or more bolts 412. The housing member 410 includes a bore 414 defined therethrough that houses the engagement portion 460*b* therein.

As shown in FIGS. 10-14, the drive shaft 119 includes a coupling member 500 at its distal end which is coupled to a drive linkage 502 interconnecting the drive shaft 119 of shaft assembly 200 and the drive screw 460 of end effector 400. The coupling member 500 includes a distal ball joint 500*a* and a pair of opposing proximal surfaces 500*b* located at a neck portion thereof. The drive linkage, disposed within the housing portion 410, has a drive link 502 which is off-axis with respect to the drive screw 460. In particular, the longitudinal axis defined by the drive link 502 is at a non-parallel (e.g., non-zero angle) angle with respect to a longitudinal axis defined by the drive screw 460. In embodiments, the drive link 502 may be disposed along the same longitudinal axis as the drive screw 460.

The drive link 502 includes a proximal engagement portion 501 and a distal engagement portion 503. The proximal engagement portion 501 is configured to be engaged by the ball joint 500*a* of coupling member 500, and the distal engagement portion 503 is dimensioned and configured to engage the proximal engagement portion 460*b* of drive screw 460. In particular, the engagement portion 501 includes a socket 501*a*, which is configured and dimensioned to interface with the ball joint 500*a*. The drive link 502 also includes a pair of opposing surfaces 501*b* defining an opening 501*c*. The ball joint 500*a* of coupling member 500 is inserted into the socket 501*a* of proximal engagement portion 501 allowing the respective surfaces 500*b* and 501*b* to abut each other and be in mechanical cooperation with one another. The mechanical coupling of the ball joint 500*a* and the socket 501*a* inhibits disengagement of the drive link 502 from the coupling member 500, and the abutment of the surfaces 500*b* and 501*b* allows for transfer of rotational motion of the coupling member 500 to the drive link 502.

Figure 11:
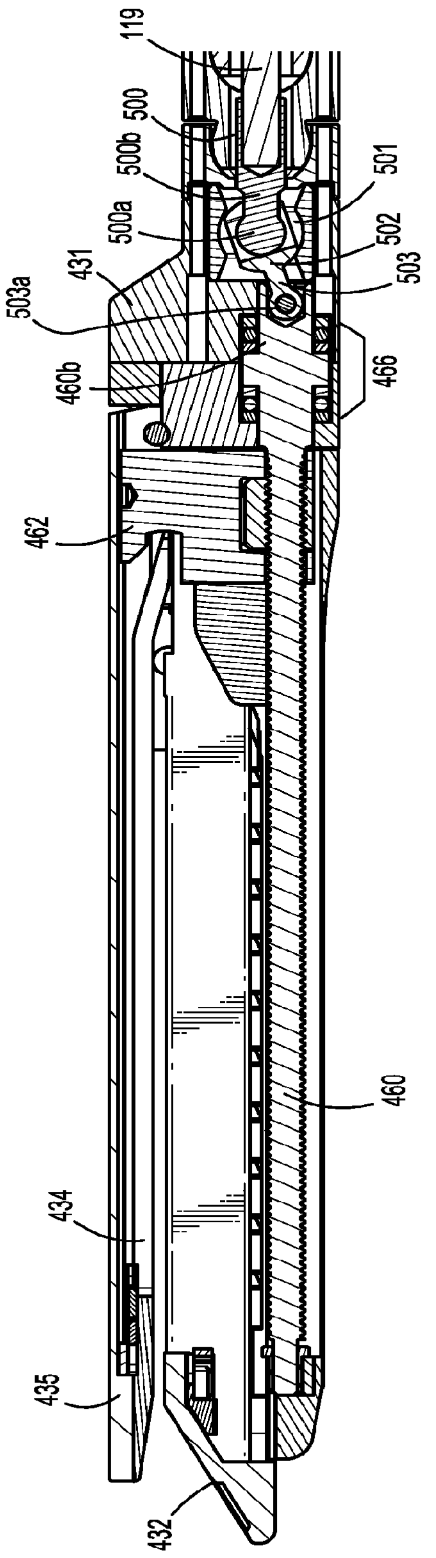
FIG. 11 is a side, cross-sectional view of the end effector of FIG. 1, according to the present disclosure.
Figure 12:
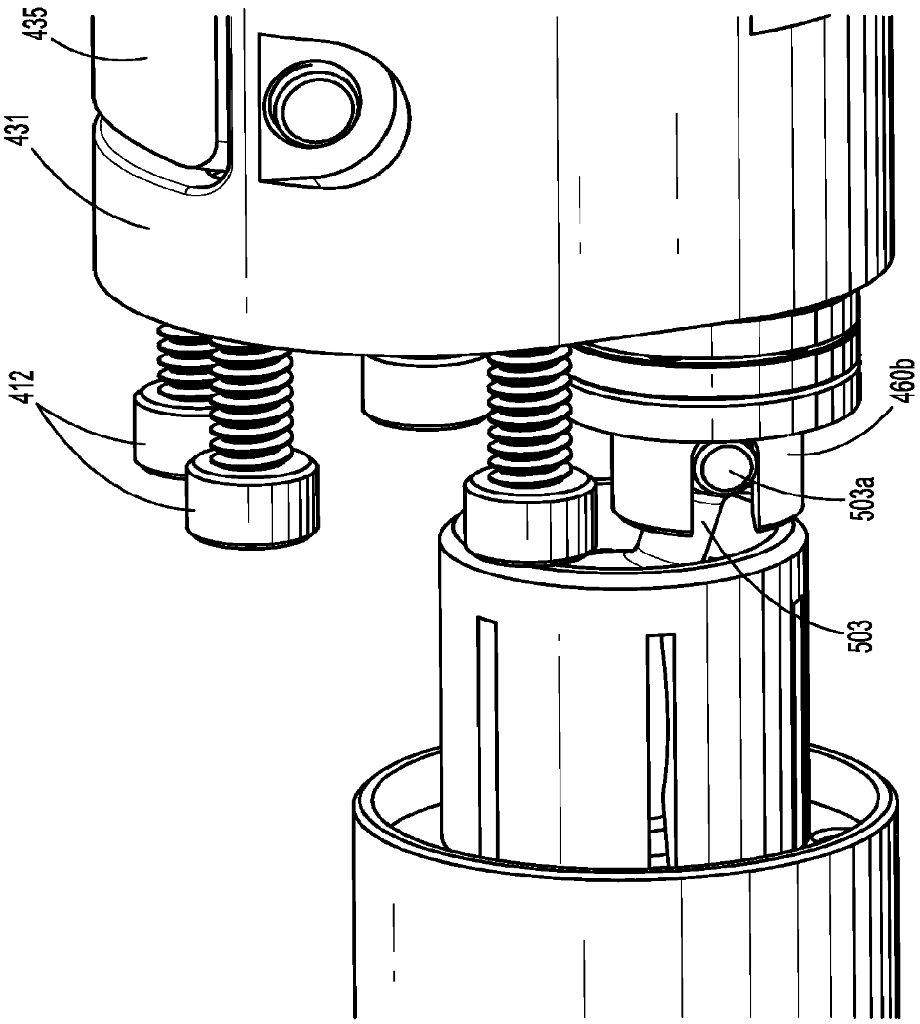
FIG. 12 is a side, partially exploded view of a coupling member of the end effector of FIG. 1, according to the present disclosure.
Figure 13:
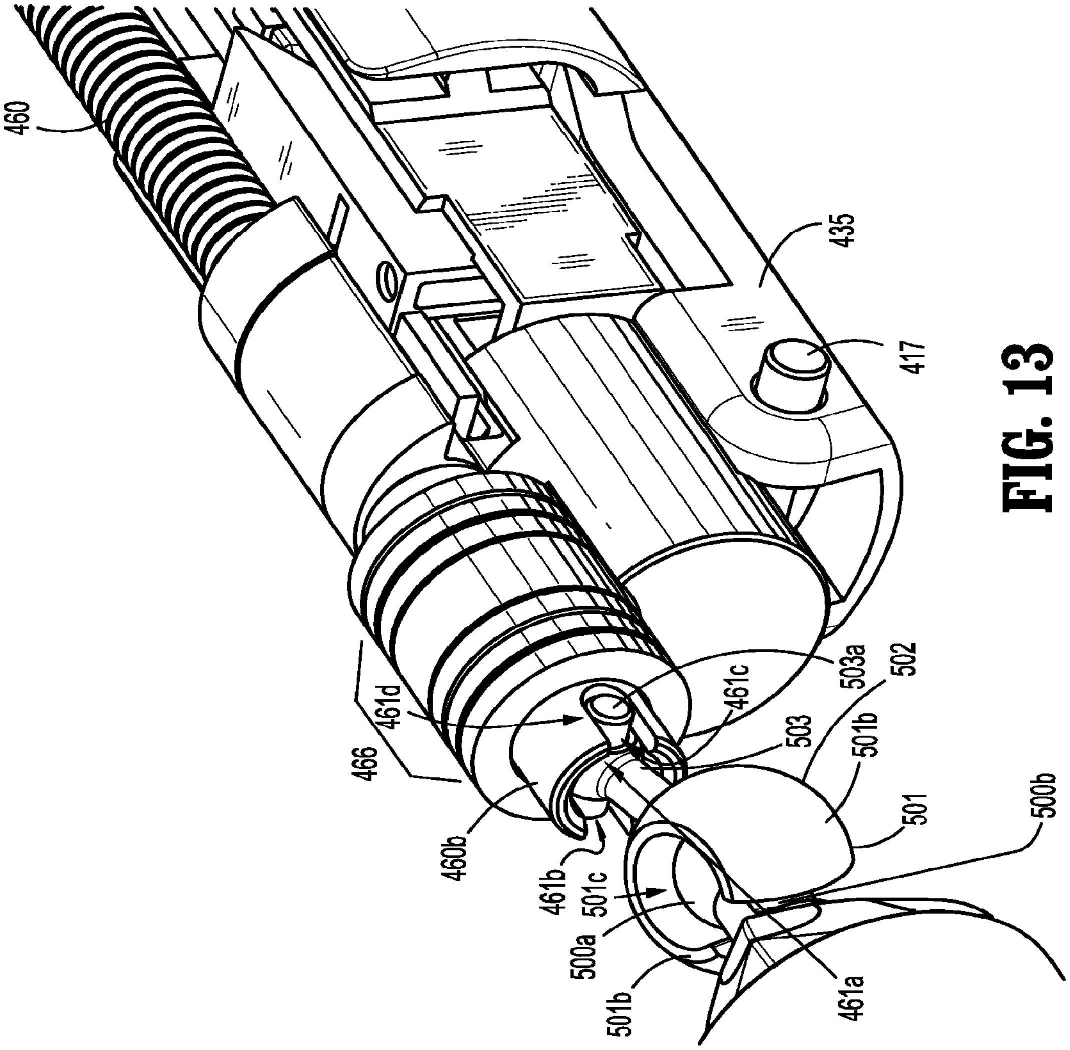
FIG. 13 is a perspective, partially exploded view of the coupling member of the end effector of FIG. 1, according to the present disclosure.
Figure 14:
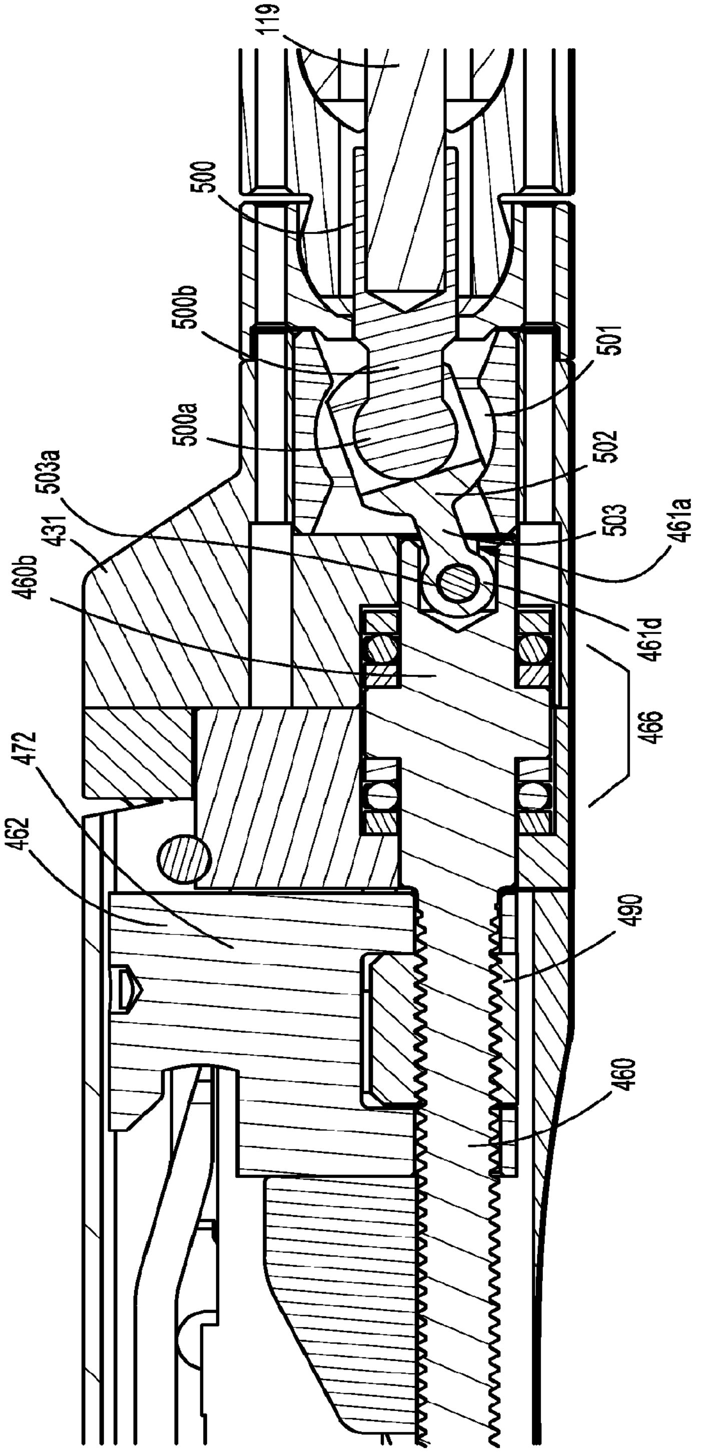
FIG. 14 is a side, cross-sectional view of the coupling member of the end effector of FIG. 1, according to the present disclosure.

As seen in FIGS. 11-13, the distal engagement portion 503 of drive link 502 includes a pin 503*a* at its distal end, extending transversely therethrough, and being configured and dimensioned to interface with the engagement portion 460*b* of the drive screw 460. The engagement portion 460*b* of drive screw 460 may be configured and dimensioned as a clevis to interface with the pin 503*a*. In particular, the engagement portion 460*b* includes a bore 461*a* at its distal end for insertion of the engagement portion 503 thereinto. As shown in FIG. 13, the engagement portion 460*b* also includes a pair of diametrically opposed openings 461*b* and 461*c* defined at the sides of the bore 461*a* thereby forming a clevis 461*d*. The openings 461*b* and 461*c* may be formed as slits having an entry at the distal end thereof as shown in FIG. 13, allowing the pin 503*a* to be inserted thereinto.

With reference to FIGS. 10 and 11, end effector 400 further includes a drive beam 462 disposed within carrier 431. The drive beam 462 includes a vertical support strut 472 and an abutment surface 476 which engages the central support wedge 445 of actuation sled 440. The drive beam 462 also includes a cam member 480 disposed on top of the vertical support strut 472. Cam member 480 is dimensioned and configured to engage and translate with respect to an exterior camming surface 482 of anvil 434 to progressively clamp the anvil 434 against body tissue during firing.

A longitudinal slot 484 extends through the anvil 434 to accommodate the translation of the vertical strut 472. This allows the cam member 480 to travel in between the cover 435 and anvil 434 during firing. In embodiments, the anvil cover 435 may also include a corresponding longitudinal slot (not shown) formed on an underside thereof and is secured to an upper surface of anvil 434 to form a channel therebetween.

The drive beam 462 includes a distal retention foot 488*a* and a proximal retention foot 488*b*, each having a bore 489*a* and 489*b* defined therethrough. The bores 489*a* and 489*b* may be either threaded or smooth to provide for travel along the drive screw 460 which passes therethrough. A travel nut 490 having a threaded bore 490*a* therethrough is disposed between the distal and proximal retention feet 488*a* and 488*b*. The drive screw 460 is threadably coupled to the travel nut 490 through the bore 490*a*, such that as the drive screw 460 is rotated, the travel nut 490 travels in a longitudinal direction along the longitudinal axis defined by the drive screw 460 and also engaging the feet 488*a* and 488*b*.

In use, as the drive screw 460 is rotated in a clock-wise direction, the travel nut 490 and the drive beam 462 travel in a distal direction closing the anvil 434 as the cam member 480 pushes down on the camming surface 482 thereof. The drive beam 462 also pushes the sled 440 in the distal direction, which then engages the pushers 437 via the cam wedges 444 to eject the fasteners 433. The drive beam 462 may be made of any suitable first material including, but not limited to, plastics, metals, and combinations thereof. The travel nut 490 may be made of any suitable second material also including, but not limited to, plastics, metals, and combinations thereof. The first and second materials may be either same or different. In embodiments, the drive beam 462 may include a single retention foot with a threaded bore defined therethrough, which is threadably coupled to the drive screw 460.

With reference to FIG. 10, the drive beam 462 also includes a knife blade 474 for dissecting the fastened tissue. The knife blade 474 travels slightly behind actuation sled 440 during a stapling procedure to form an incision between the rows of fastener body tissue. As the drive beam 462 is driven in the distal direction, the abutment surface 476 of the vertical strut 472 pushes the sled 440 in the distal direction to eject the fasteners 433 and simultaneously dissect tissue with the knife blade 474. The knife blade 474 and the drive beam 462 travel through the longitudinal slots 484 and 485. The drive beam 462 closes the anvil as it is driven in the distal direction and also pushes the sled 440, which, in turn, ejects the fasteners 433 ahead of the knife blade 474. As the fasteners 433 are ejected they are deformed again the tissue-contacting (e.g., underside) surface of the anvil 434 having a plurality of anvil pockets (not shown).

Figure 15:
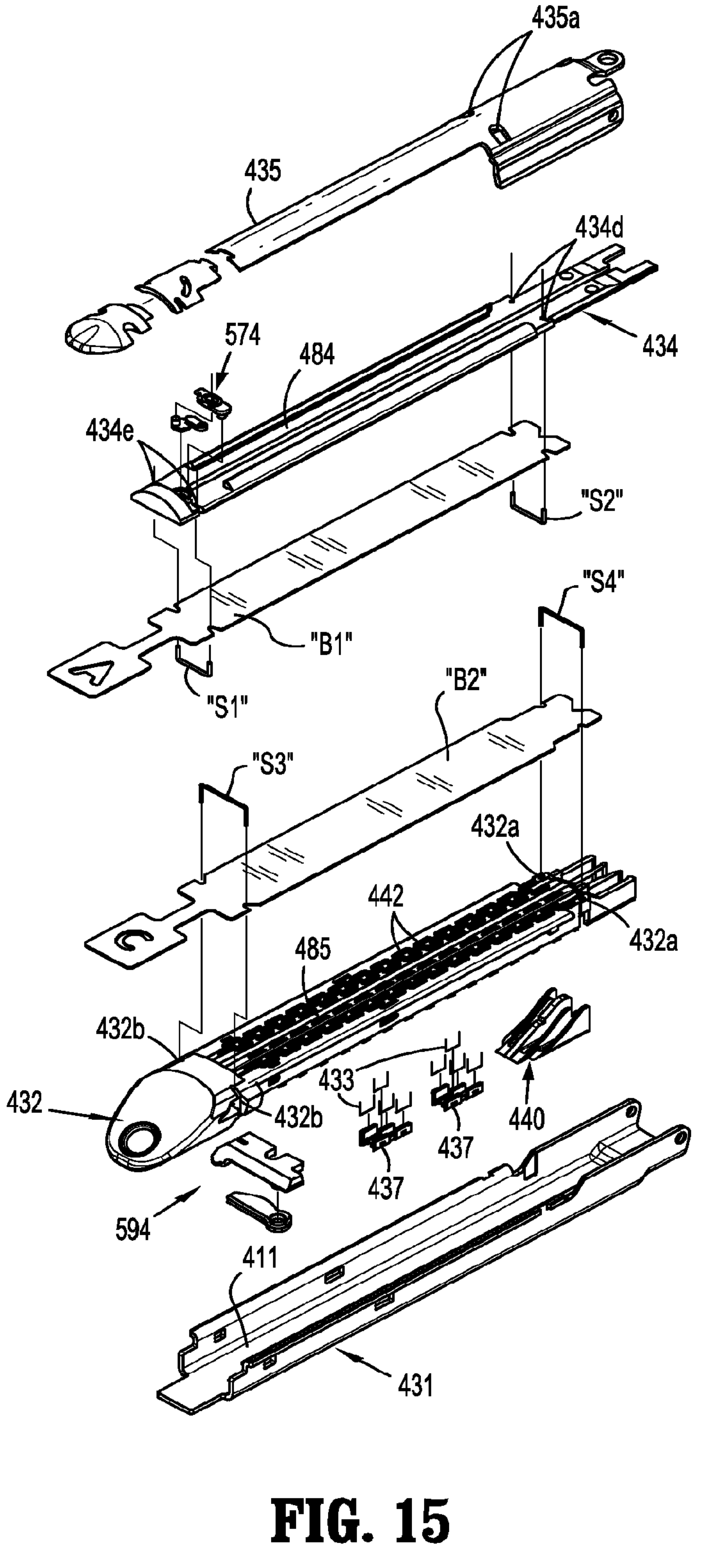
FIG. 15 is a top, perspective view, with parts separated, of the end effector including a surgical cartridge buttress secured to a tissue contacting surface thereof according to the present disclosure.
Figure 16:
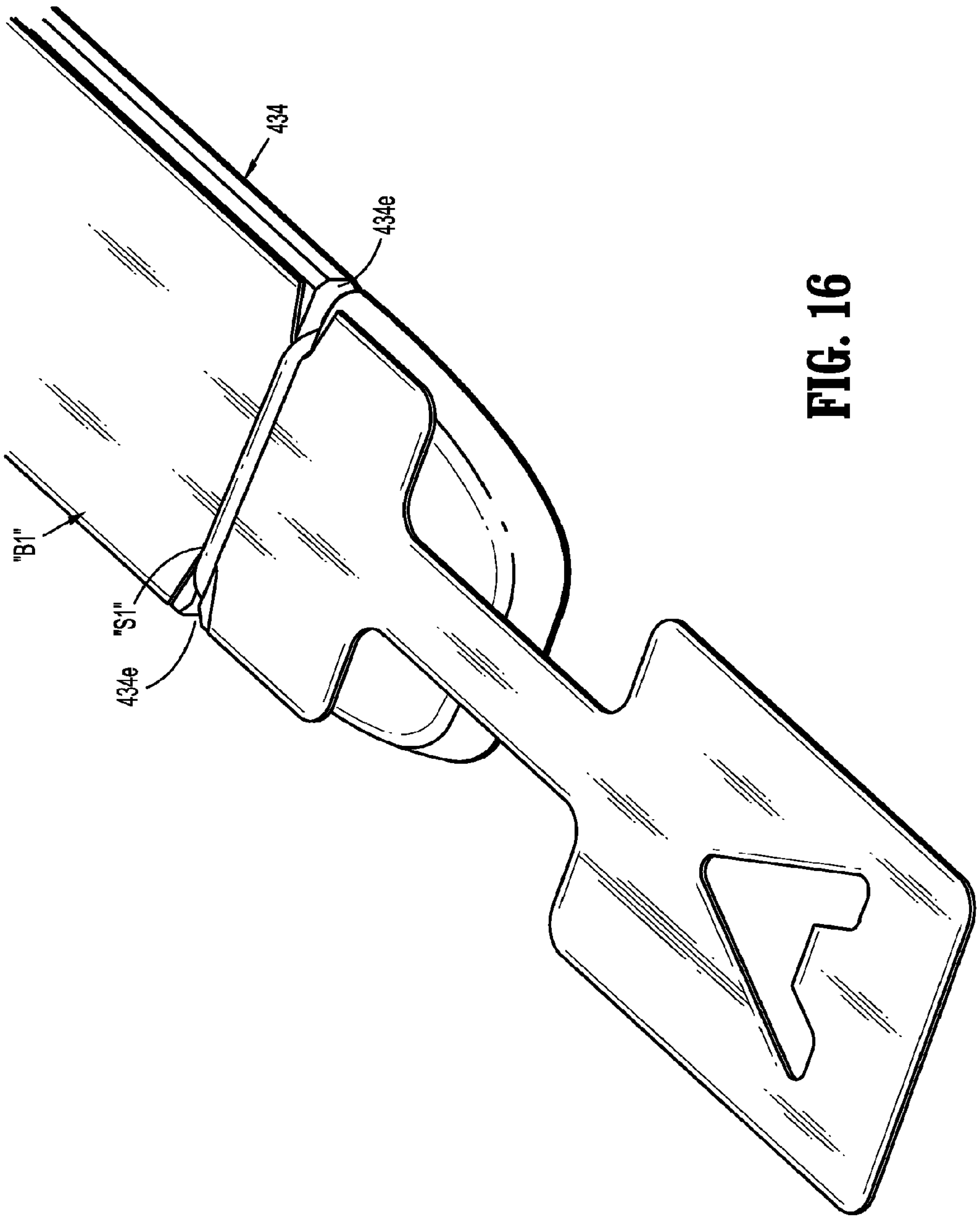
FIG. 16 is an enlarged perspective view of a distal end of an anvil assembly of the end effector illustrating a surgical anvil buttress operatively secured to a tissue contacting surface thereof according to the present disclosure.
Figure 17:
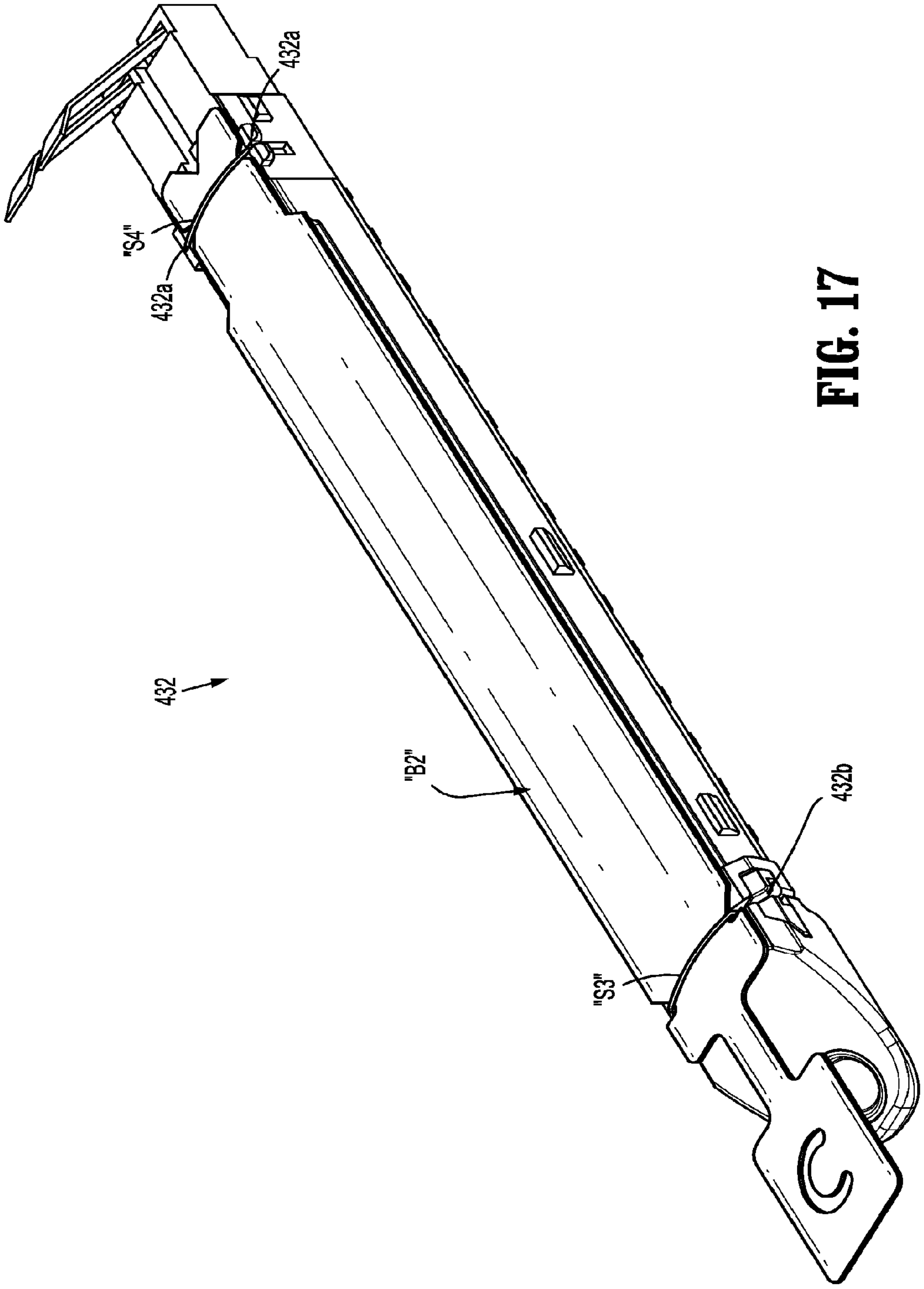
FIG. 17 is an enlarged perspective view of a cartridge assembly of the end effector illustrating a surgical cartridge buttress secured to a tissue contacting surface thereof according to the present disclosure.

FIG. 15 shows another embodiment of the end effector 400. The anvil 434 defines a proximal pair of recesses **434*d* formed near a proximal end of anvil 434 and disposed, one each of the opposite sides of longitudinal slot 484. Anvil 434 also defines a distal pair of recesses 434*e* formed near a distal end of anvil 434 and disposed, one each, on opposed sides of longitudinal slot 484. In one embodiment, at least one of the recesses of each of the proximal pair of recesses 434*d* and the distal pair of recesses 434*e* may be non-circular and constricting, or has a reduced width dimension, so as to frictionally engage and/or pinch an anchor "S". Additionally, anvil cover 435 defines a pair of opposed recesses 435*a* formed therein which align with the proximal pair of recesses 434*d* formed in anvil 434 when anvil cover 435 is assembled with anvil 434**.

The anvil 434 further includes a surgical anvil buttress "B1", pledget or any other surgical implant, operatively secured to a lower surface or tissue contacting surface of anvil 434, by an anchor "S", to overlie at least some of anvil pockets and/or at least a portion of a length of longitudinal slot 484. As used herein the term anchor is understood to include and is not limited to sutures, threads, tethers, straps, bands, lines, wires, cables, fasteners, tacks or any other material suitable for the intended purpose disclosed herein. In certain embodiments, the anchor is an extension of the staple line reinforcement material discussed below. The anchor may comprise an integral part of the staple line reinforcement material, or may be formed from the same or a similar material and attached to the staple line reinforcement material. In particular, an anchor "S" is cinched around a proximal portion of surgical anvil buttress "B1" and each of the proximal pair of recesses **434*d* and an anchor "S" is cinched around a distal portion of the surgical anvil buttress "B1" and each of the distal pair of recesses 434*e***.

Surgical anvil buttress "B1" includes a proximal pair of notches formed in side edges aligned with the proximal pair of recesses **434*d* of anvil 434, a distal pair of notches formed in side edges thereof aligned with the distal pair of recesses 434*e* of anvil 434, and a proximal notch formed in a proximal edge thereof aligned with longitudinal slot 484 when surgical anvil buttress "B1" is secured to anvil 434. Surgical anvil buttress "B1" further includes a tongue or tab extending from a distal edge thereof to facilitate with the attachment of surgical anvil buttress "B1" to anvil 434 during the assembly process. It is contemplated that the tongue is removed from surgical anvil buttress "B1" following securement of surgical anvil buttress "B1" to anvil 434** and prior to packaging or shipment.

As seen in FIGS. 18-24, anvil 434 further includes an anvil release assembly 574 disposed between anvil 434 and anvil cover 435 at a location in operative registration with the distal pair of recesses **434*e*. Release assembly 574 includes a guide plate 575 defining an arcuate slot 575*a* formed therethrough. The slot 575*a*** is configured and dimensioned to receive a tool (not shown) therethrough as discussed in greater detail below.

Figure 18:
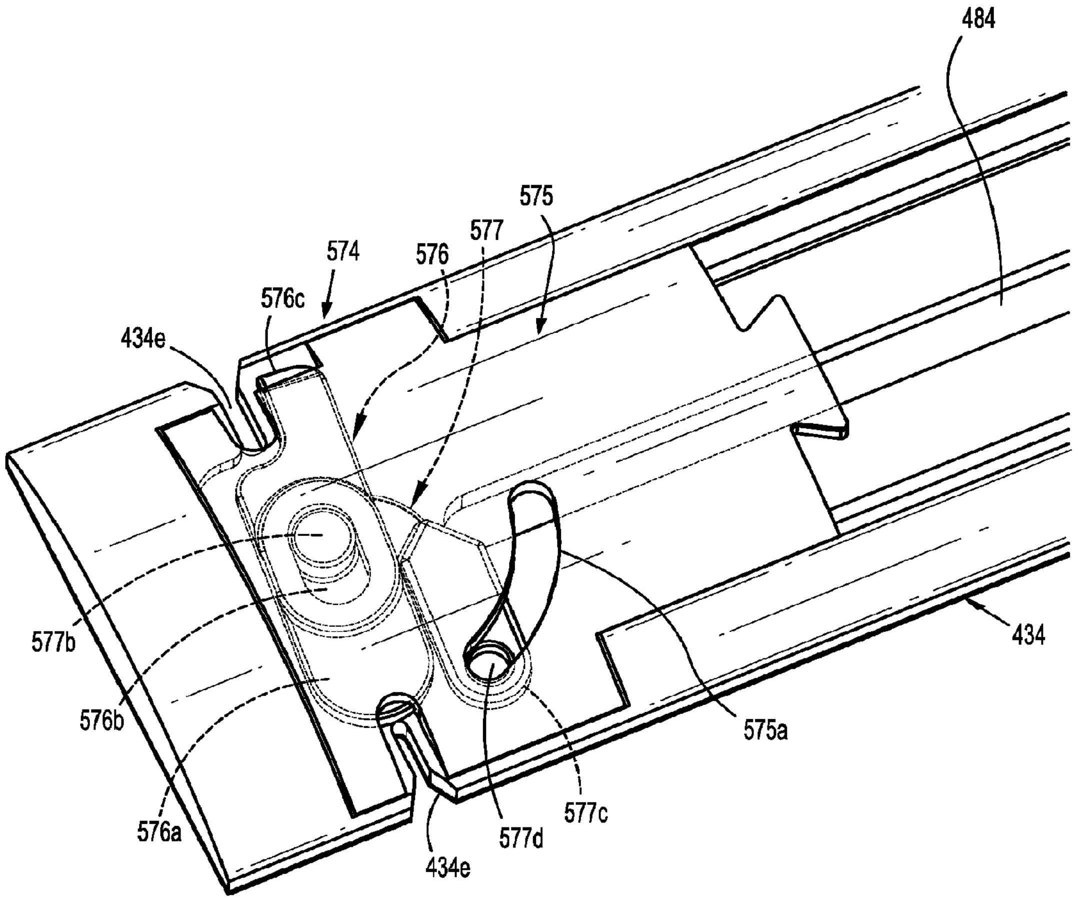
FIG. 18 is a top, perspective view of a distal end of an anvil assembly of the end effector including a suture release assembly shown in an open configuration according to the present disclosure.
Figure 19:
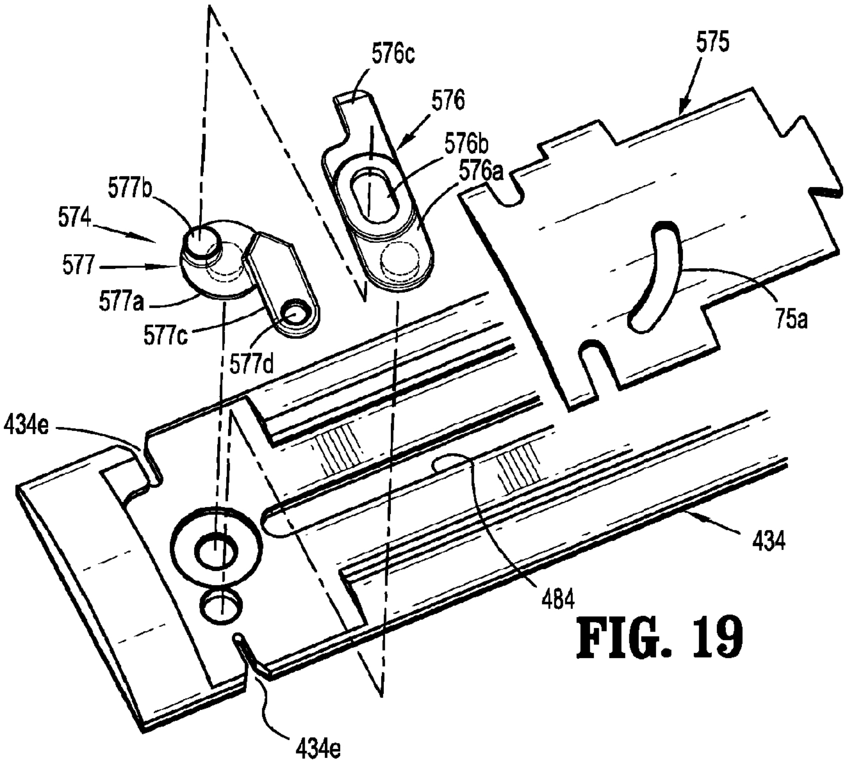
FIG. 19 is a top, perspective view of the anvil assembly of FIG. 18, illustrating the parts of the suture release assembly thereof separated according to the present disclosure.
Figure 20:
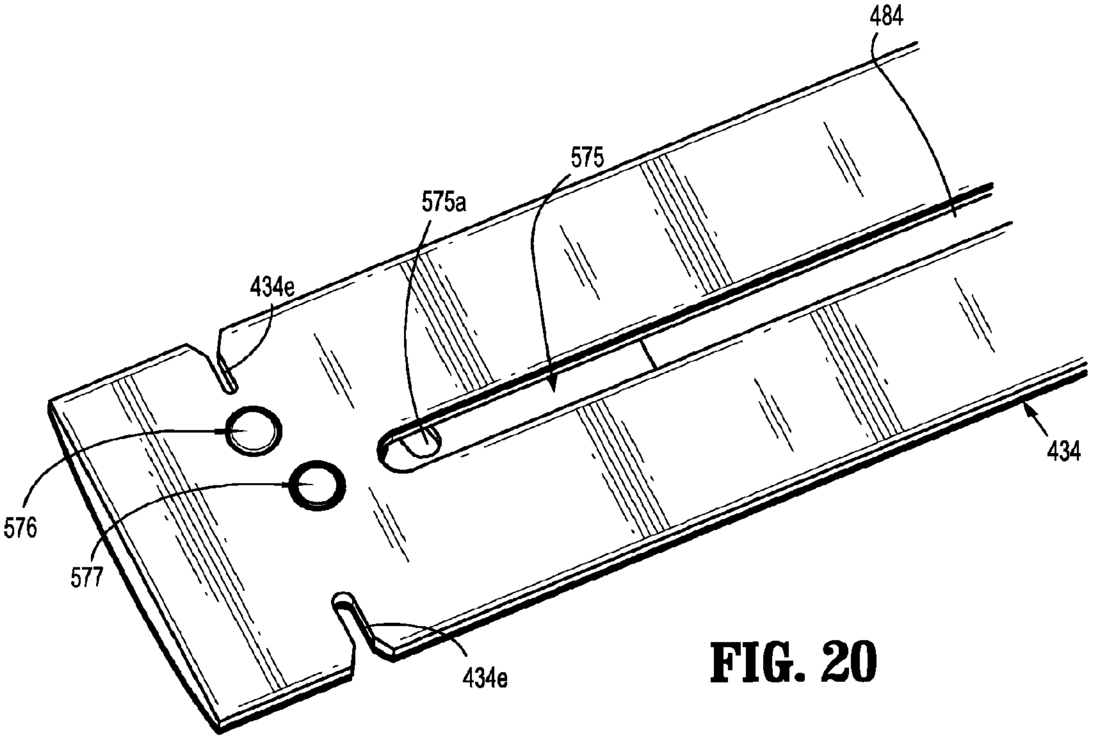
FIG. 20 is a bottom, perspective view of the anvil assembly of FIG. 18 according to the present disclosure.

With reference to FIGS. 18-20, release assembly 574 further includes a lock or anchor bar 576 pivotally connected to anvil 434 and/or optionally anvil cover 435. Anchor bar 576 includes a body portion **576*a* defining an elongate channel or slot 576*b* therein and a finger 576*c* extending from an edge thereof. Finger 576*c* is in operative registration with one of the distal pair of recesses 434*e***, preferably, the one of the distal pair of recesses having the relatively larger width dimension.

Suture release assembly 574 further includes an anchor bar actuation member 577 pivotally connected to anvil 434 and/or optionally anvil cover 435. Actuation member 577 includes an eccentric cam **577*a* defining a central axis of rotation about which actuation member is permitted to rotate. Actuation member 577 includes a nub or boss 577*b* extending from a surface of eccentric cam 577*a* in a direction substantially parallel to and offset a radial distance from the central axis of rotation of eccentric cam 577*a*. Boss 577*b* is slidably and rotatably disposed in elongate slot 576*b* of anchor bar 576. Actuation member 577 further includes a release bar 577*c* extending substantially tangentially from eccentric cam 577*a* from a side substantially opposite to Boss 577*b*. Release bar 577*c* defines a pin 577*d* formed thereon which is in registration with the arcuate slot 575*a* of guide plate 575. In operation, as eccentric cam 577*a* is rotated, pin 577*d* of release bar 577*c* follows along the path of arcuate slot 575*a* of guide plate 575**.

Figure 21:
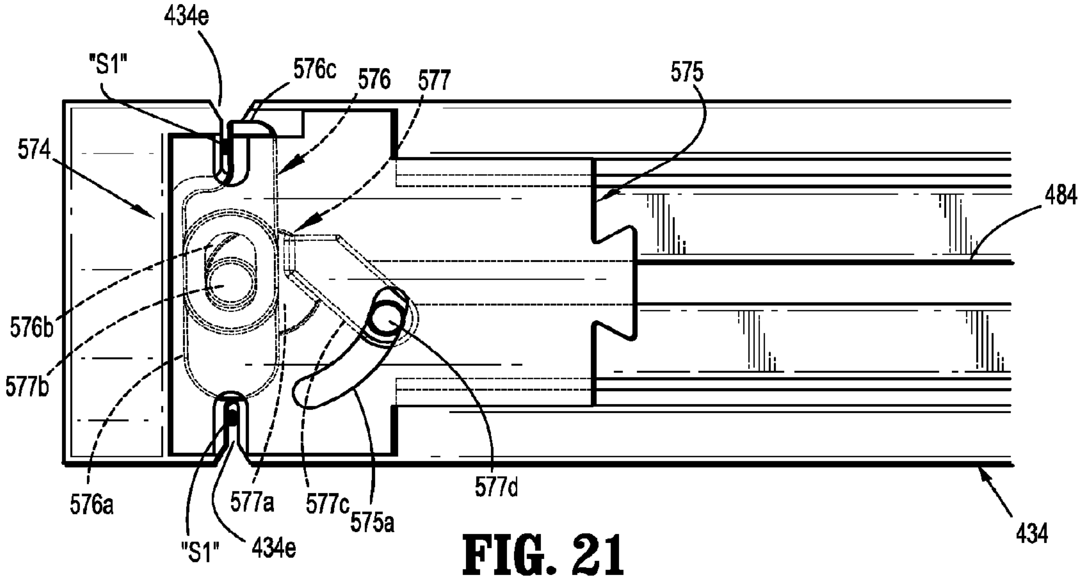
FIG. 21 is a top, plan view of the anvil assembly of FIG. 18, illustrating the suture release assembly thereof in the closed configuration according to the present disclosure.
Figure 22:
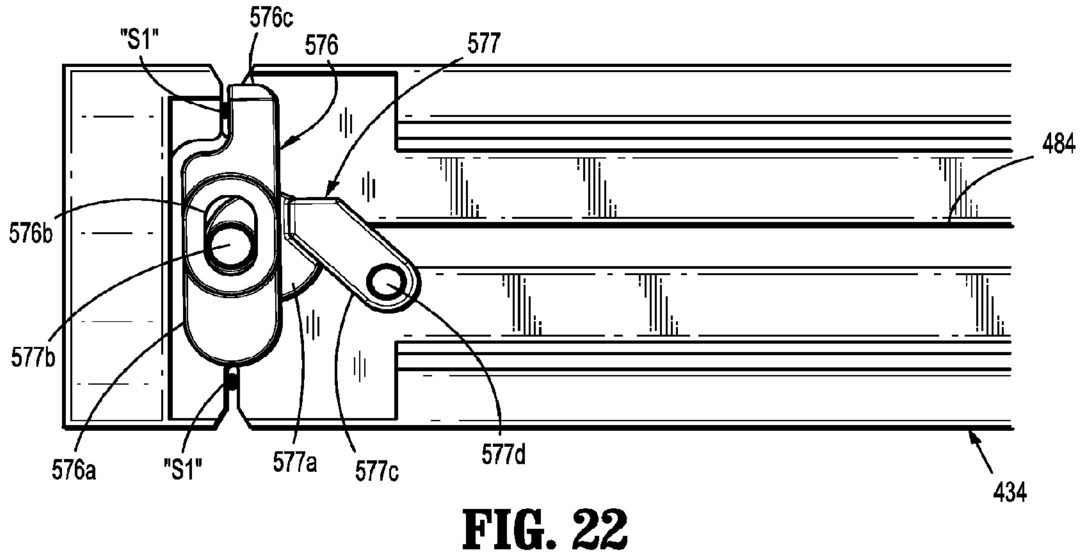
FIG. 22 is a top, plan view of the anvil assembly of FIG. 18, with a retainer removed therefrom.

As seen in FIGS. 21 and 22, suture release assembly 574 includes a locking or anchoring configuration wherein finger **576*c* of anchor bar 576 extends into or overlies the respective one of the pair of distal recesses 434*e* in operative registration therewith, release bar 577*c* of actuation member 577 extends across longitudinal slot 484 of anvil 434, and pin 577*d* of release bar 577*c* is disposed at or near a first end of arcuate slot 575*a* of guide plate 575. It is contemplated that suture release assembly 574 may include a friction fit or snap fit feature for maintaining and/or retaining suture release assembly 574 in the locking or anchoring configuration at all times following the manufacturing/assembly process and prior to a complete firing of instrument 100**.

Figure 23:
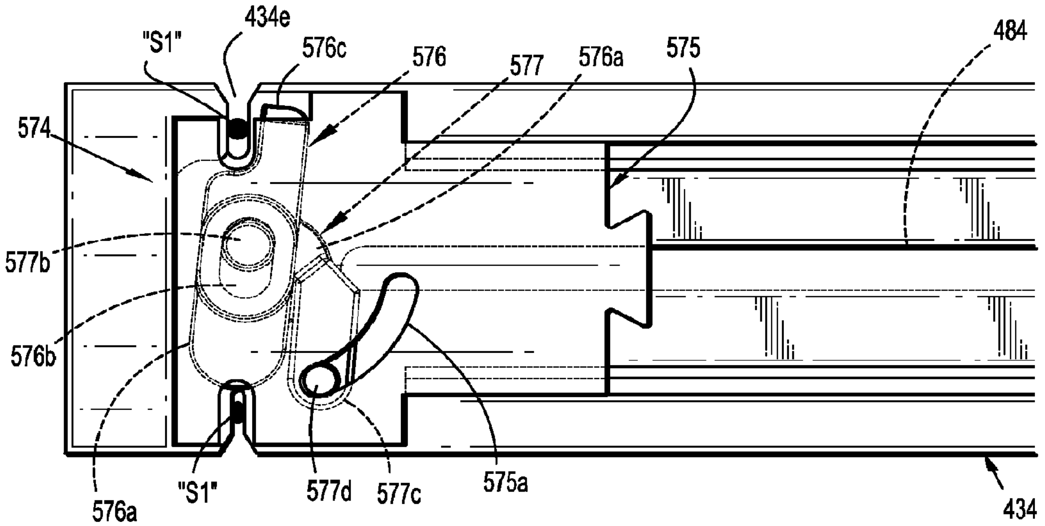
FIG. 23 is a top, plan view of the anvil assembly of FIG. 18, illustrating the suture release assembly thereof in the open configuration according to the present disclosure.
Figure 24:
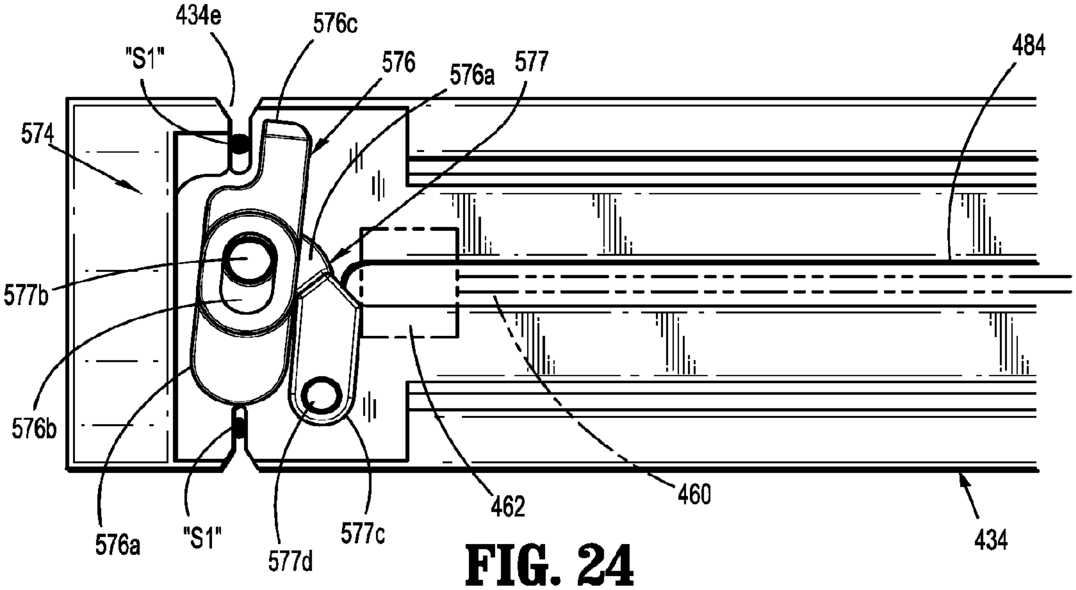
FIG. 24 is a top, plan view of the anvil assembly of FIG. 18, with a retainer removed therefrom according to the present disclosure.
Figure 25:
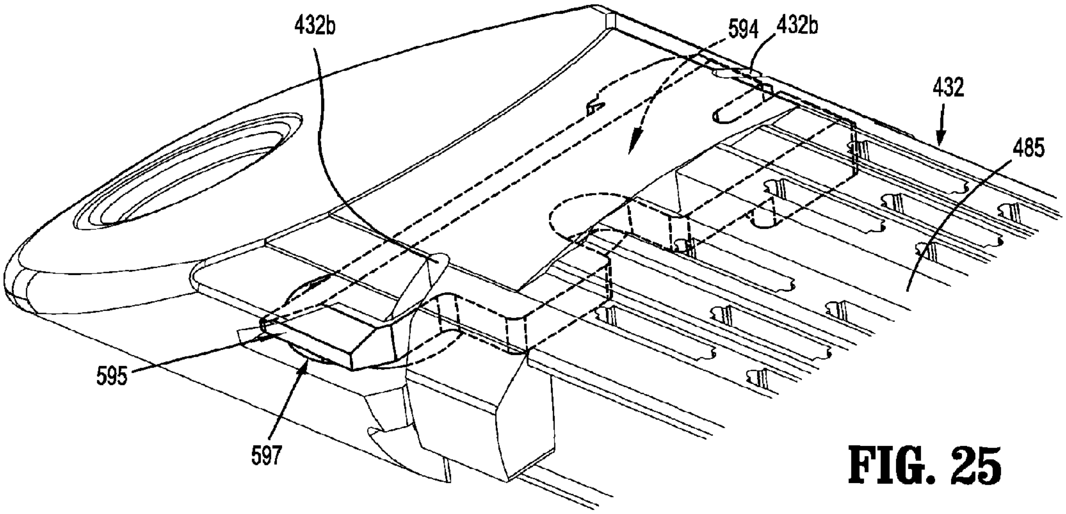
FIG. 25 is a top, perspective view of a distal end of a cartridge assembly of the end effector including a suture release assembly according to the present.

As seen in FIGS. 23 and 24, suture release assembly 574 includes an open or release configuration wherein finger **576*c* of anchor bar 576 does not extend into or overlie the respective one of the pair of distal recesses 434*e* in operative registration therewith, release bar 577*c* of actuation member 577 does not extend across longitudinal slot 484 of anvil 434, and pin 577*d* of release bar 577*c* is disposed at or near a second end of arcuate slot 575*a* of guide plate 575**.

Suture release assembly 574 may be used by a manufacturer during the assembly process of instrument 100 to secure, with a surgical suture or tether, a surgical anvil buttress "B" to a tissue contacting surface of the anvil 434, and by the end user of instrument 100 to automatically release or free the surgical anvil buttress "B" from the tissue contacting surface of the anvil 434 upon a complete firing of the instrument 100.

With reference to FIGS. 21-24, during the manufacturing process, with suture release assembly 574 in the open or release configuration (FIGS. 23 and 24), a surgical anvil buttress "B" is laid over the tissue contacting surface of anvil 434. Then, a first end of a surgical suture "S1" is inserted into one of the pair of distal recesses **434*e* and a second end of surgical suture "S1" is extended across the surgical anvil buttress "B1" (see FIG. 15) and inserted into the other of the pair of distal recesses 434*e*. It is contemplated that the first end of surgical suture "S1" may include a knot, stop or the like (not shown) sized so as to not pass through the narrower recess of the distal pair of recesses 434*e***.

With the second end of the surgical suture "S1" disposed in the pair of distal recesses **434*e*, and with the surgical suture "S1" pulled taught across the surgical anvil buttress "B", a tool (not shown) is inserted through arcuate slot 575*a* of guide plate 575 and engaged with an opening provided in the pin 577*d* of release bar 577*c*. With reference to FIGS. 21 and 22, the tool is then manipulated to move through or along arcuate slot 575*a* of guide plate 575, thereby actuating or moving release bar 577*c* and rotating eccentric cam 577*a*. As eccentric cam 577*a* is rotated, boss 577*b* is rotated around the pivot axis of eccentric cam 577*a* and acts on the walls of elongate slot 576*b* of anchor bar 576 thereby causing anchor bar 576 to pivot. As anchor bar 576 is pivoted, finger 576*c* thereof is caused to extend into or overlies one of the distal recesses 434***e* and to pinch the second end of the surgical suture disposed therewithin. Meanwhile, release bar 577*c* has been moved to a position extending across longitudinal slot 484 of anvil 434. Suture release assembly 574 is now in the locking or anchoring configuration, as described above. The distal recess 434*e* that cooperates with the finger 576*c* is desirably relatively wide so as to allow the suture "S1" to easily pass into and out of the recess 434*e* when the anchor bar 576 is away from the recess 434*e*. The other distal recess 434*e*, arranged on the opposite lateral side of the anvil 434, may be the same size, or may be small enough to cinch the suture "S1" and hold the suture in place to facilitate assembly.

In operation, with surgical anvil buttress "B1" secured against the lower surface of anvil 434, during firing of instrument 100, as actuation sled 440 is advanced from a proximal-most position to a distal-most position, knife blade 474 slices through a central section of the proximal suture "S2", thereby freeing the proximal end of the surgical anvil buttress "B1" from anvil 434. During use, as the firing stroke of instrument 100 is nearing completion and as actuation sled 440 approaches a distal end of longitudinal slot 484 of anvil 434, as seen in FIG. 24, drive beam 462 being driven by the draft screw 460 contacts release bar 577*c*, urging release bar 577*c* and, in turn, eccentric cam 577*a* to rotate about the pivot axis thereof. As eccentric cam 577*a* is rotated, Boss 577*b* is rotated around the pivot axis of eccentric cam 577*a* and acts on the walls of elongate slot 576*b* of anchor bar 576 thereby causing anchor bar 576 to pivot. As anchor bar 576 is pivoted, finger 576*c* thereof is caused to move away from the relatively wider distal recess 434*e* and to release the second end of the surgical suture "S" disposed therewithin. With the second end of surgical suture "S" released or free, the distal end of the surgical anvil buttress "B1" is free to separate from the tissue contacting surface of anvil 434.

With reference to FIG. 15, cartridge assembly 432 defines a proximal pair of recesses 432*a* formed near a proximal end thereof and disposed, one each, on opposed sides of longitudinal slot 485. Cartridge assembly 432 further defines a distal pair of recesses 432*b* formed near a distal end thereof and disposed, one each, on opposed sides of longitudinal slot 485. In one embodiment, at least one of the recesses of each of the proximal pair of recesses 432*a* and the distal pair of recesses 432*b* is preferably non-circular and constricting or otherwise arranged so as to frictionally engage and/or pinch an anchor "S."

Cartridge assembly 432 further includes a surgical cartridge buttress "B2", pledget or any other surgical implant, operatively secured to an upper surface or tissue contacting surface of cartridge assembly 432, by anchors "S3" and "S4", to overlie at least some of fastener pockets 442 and/or at least a portion of a length of longitudinal slot 485. In particular, an anchor "S4" is cinched around a proximal portion of surgical cartridge buttress "B2" and each of the proximal pair of recesses 432*a* and an anchor "S3" is cinched around a distal portion of the surgical cartridge buttress "B2" and each of the distal pair of recesses 432*b*.

In one particular embodiment, a first end of each anchor "S" includes a knot, stop or the like (not shown) sized so as to not pass through one recess of the proximal pair of recesses 432*a* and a second end of each anchor "S" passes over, and transversely across, surgical cartridge buttress "B2", at least once, and back through the other recess of the proximal pair of recesses 432*a*. For example, the second end of each anchor "S" may be pinched or cinched in the other recess of the proximal pair of recesses 432*a* so as to anchor the second end of the anchor "S" and secure the surgical cartridge buttress "B2" against the tissue contacting surface of cartridge assembly 432. Similarly, an anchor "S3" is used to extend transversely across surgical cartridge buttress "B2" and into engagement with the distal pair of recesses 432*b*.

Surgical cartridge buttress "B2" includes a proximal pair of notches formed in side edges aligned with the proximal pair of recesses 432*a* of cartridge assembly 432, a distal pair of notches formed in side edges thereof aligned with the distal pair of recesses 432*b* of cartridge assembly 432, and a proximal notch formed in a proximal edge thereof aligned with longitudinal slot 485 when surgical cartridge buttress "B2" is secured to cartridge assembly 432. Surgical cartridge buttress "B2" further includes a tongue or tab extending from a distal edge thereof to facilitate with the attachment of surgical cartridge buttress "B2" to cartridge assembly 432 during the assembly process. It is contemplated that a width of surgical cartridge buttress "B2" may be reduced in a proximal portion thereof. It is further contemplated that the tongue is removed from surgical cartridge buttress "B2" following securement of surgical cartridge buttress "B2" to cartridge assembly 432 and prior to packaging or shipment.

As seen in FIGS. 15 and 25-29, cartridge assembly 432 further includes a cartridge release assembly 594 supported in and near a distal end of cartridge assembly 432. Release assembly 594 includes a lock or anchor bar 595 pivotally connected to cartridge assembly 432. Anchor bar 595 includes a body portion 595*a* having a finger 595*b* extending from an edge thereof. Finger 595*b* is in operative registration with one of the distal pair of recesses 432*b*, preferably, the one of the distal pair of recesses having the relatively larger width dimension.

Figure 26:
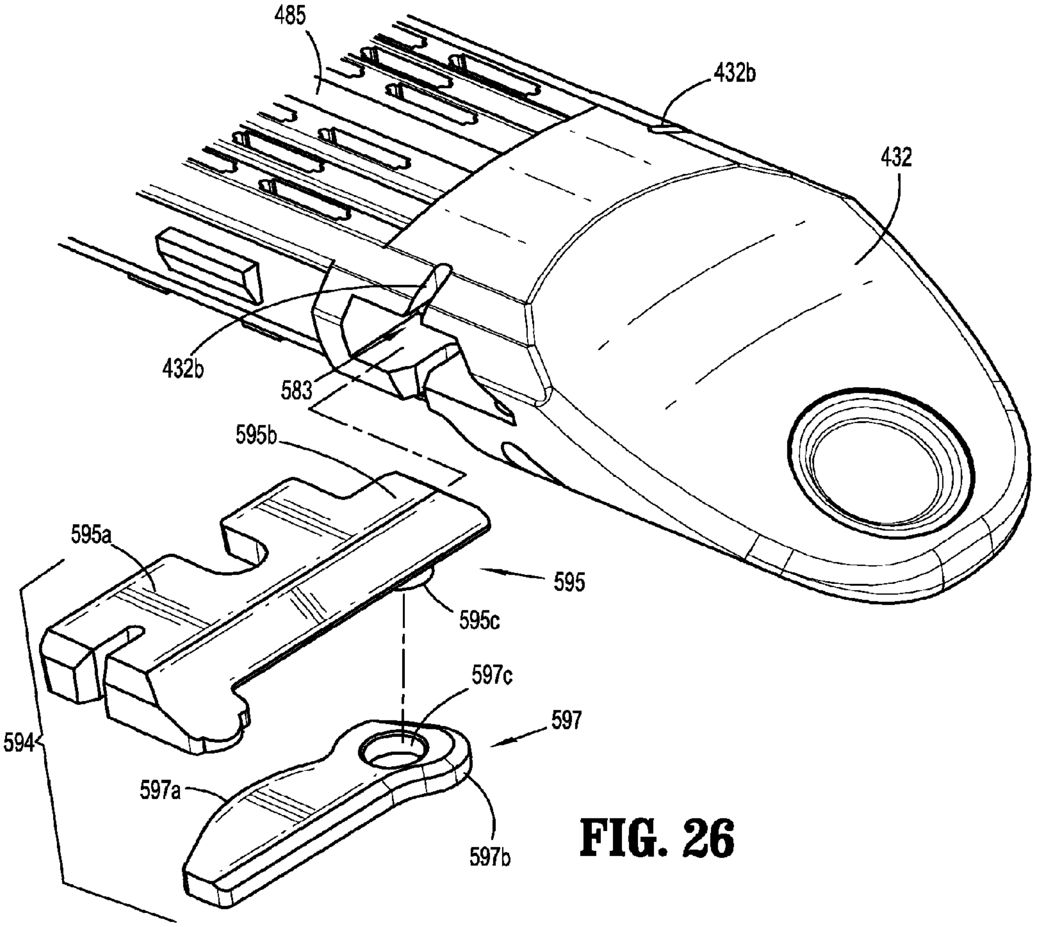
FIG. 26 is a top, perspective view of the cartridge assembly of FIG. 25, illustrating the parts of the suture release assembly thereof separated according to the present disclosure.
Figure 27:
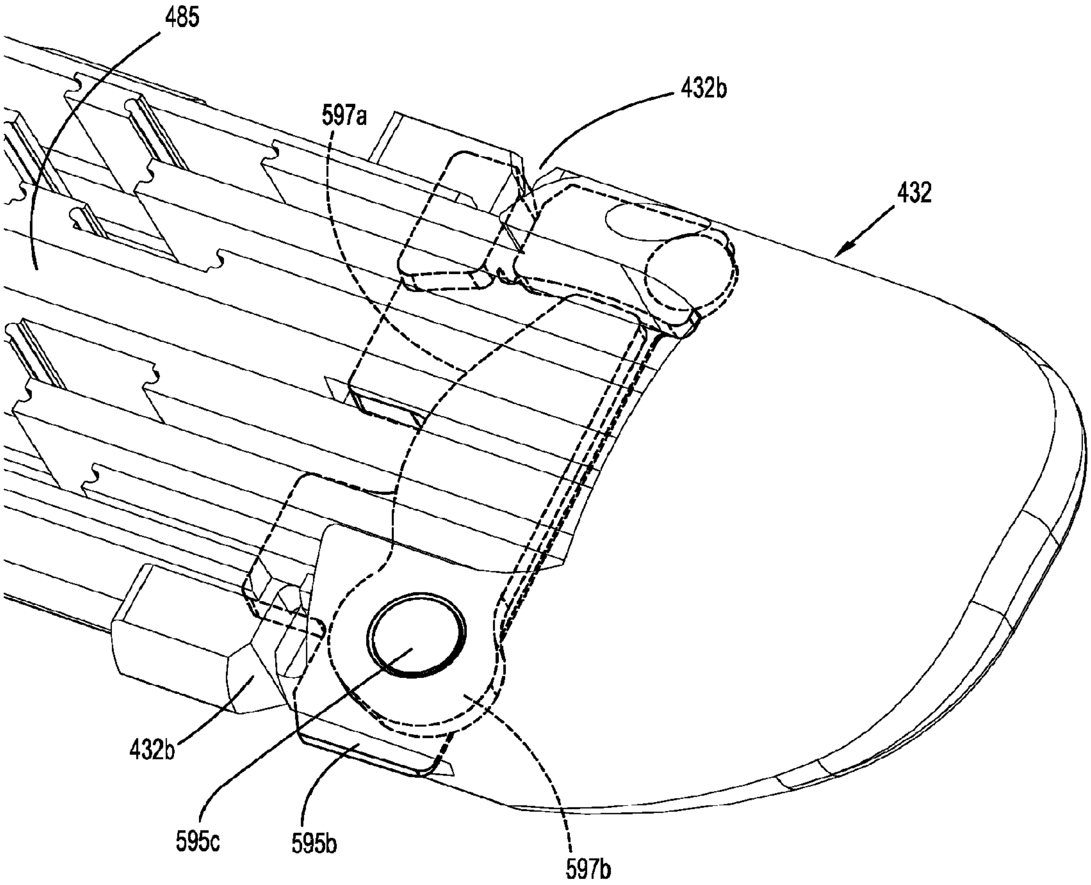
FIG. 27 is a bottom, perspective view of a distal end of the cartridge assembly of FIG. 25 according to the present disclosure.

Release assembly 594 further includes an anchor bar actuation member 597 pivotally connected to anchor bar 595 (as seen in FIGS. 26 and 27). Actuation member 597 includes a first cam surface 597*a* located along a proximal edge of actuation member 597 and extending across central longitudinal slot 485 of cartridge assembly 432, and a second eccentric cam surface 597*b* extending distally and laterally from actuation member 597 in close proximity to the one of the distal pair of recesses 432*b* that is operatively associated with finger 595*b* of anchor bar 595. First cam surface 597*a* of actuation member 597 is substantially arcuate or convex. Actuation member 597 defines an aperture or opening 597*c* configured and dimensioned to receive a pin 595*c* of anchor bar 595 therein so as to anchor bar 595 and actuation member 597 to pivot or rotate relative to one another.

In operation, rotation of actuation member 597 in a first direction, about its pivot point, results in second cam surface 597*b* abutting a surface 432*g* (see FIGS. 28 and 29) of cartridge assembly 432 and thus moving finger 595*b* at least partially over and/or across the one of the distal pair of recesses 432*b* associated therewith.

Figure 28:
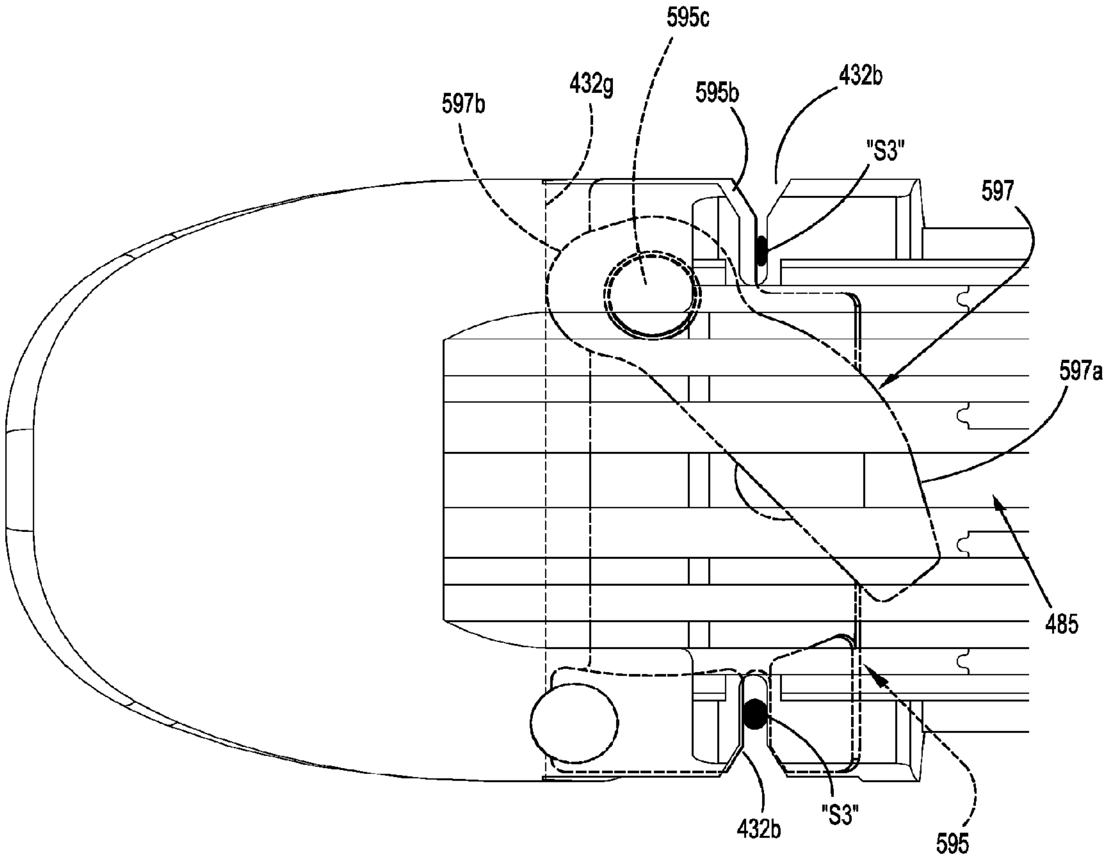
FIG. 28 is a top, plan view of the cartridge assembly of FIG. 25, illustrating the suture release assembly thereof in the closed configuration according to the present disclosure.

As seen in FIG. 28, suture release assembly 594 includes a locking or anchoring configuration wherein first cam surface 597*a* of actuation member 597 extends into and across central longitudinal slot 485 of cartridge assembly 432, wherein second cam surface 597*b* of actuation member 597 is pressed against surface 432*g* of cartridge assembly 432, and thus finger 595*b* of anchor bar 595 extends into or overlies the respective one of the pair of distal recesses 432*b* in operative registration therewith. Fastener release assembly 594 may be maintained in the locking or anchoring configuration by way of a biasing member or a detent that engages actuation member 597 in a manner so as to keep actuation member 597 in the locked or anchoring configuration. When in such a locked or anchoring configuration, the suture "S3" may be urged into recess 432*b* of cartridge assembly 432. It is contemplated that suture release assembly 594 may include a friction fit or snap fit feature for maintaining and/or retaining suture release assembly 594 in the locking or anchoring configuration at all times following the manufacturing/assembly process and prior to a complete firing of instrument 100.

Figure 29:
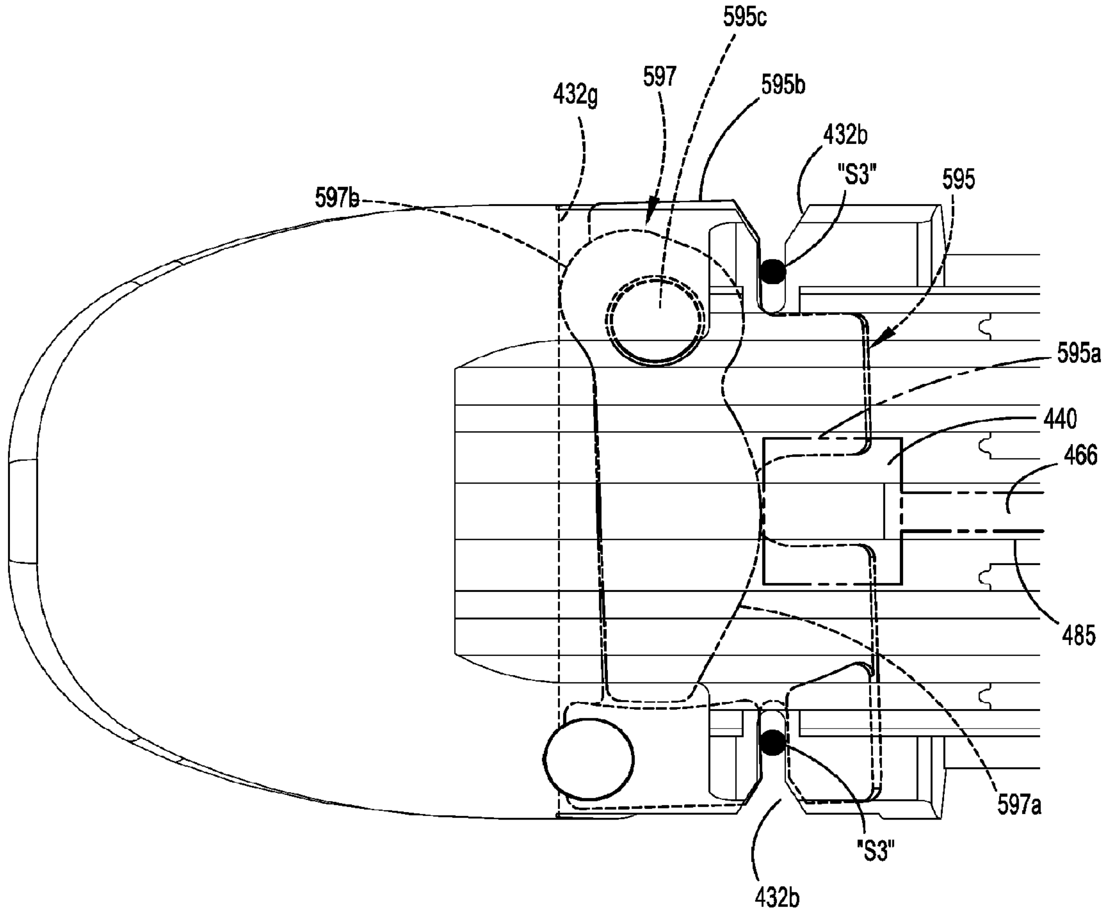
FIG. 29 is a top, plan view of the cartridge assembly of FIG. 25, illustrating the suture release assembly thereof in the open configuration according to the present disclosure.
Figure 30:
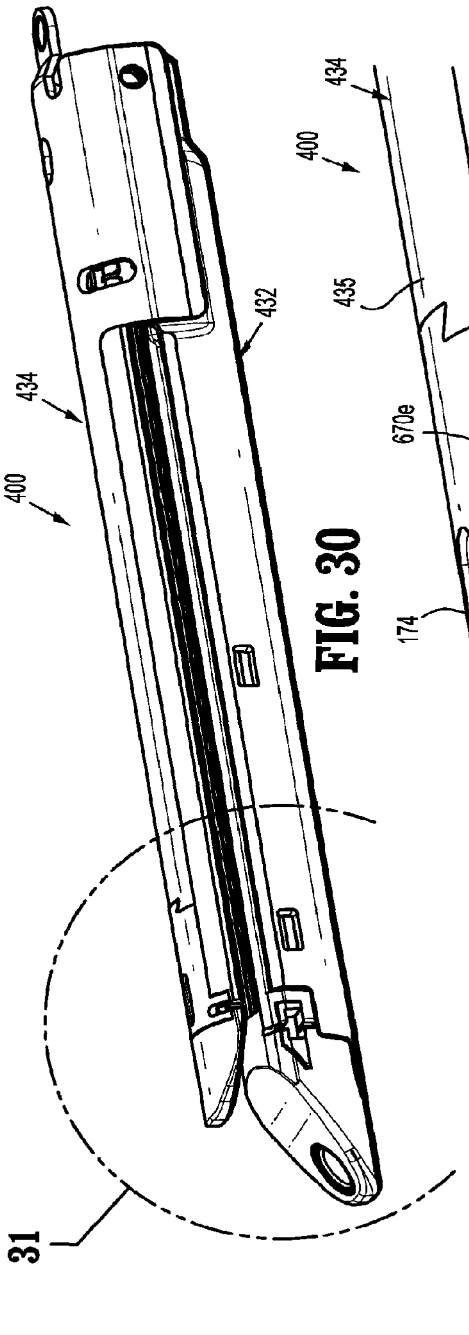
FIG. 30 is a perspective view of a distal end of a end effector including suture release assemblies according to another embodiment of the present disclosure.
Figure 31:
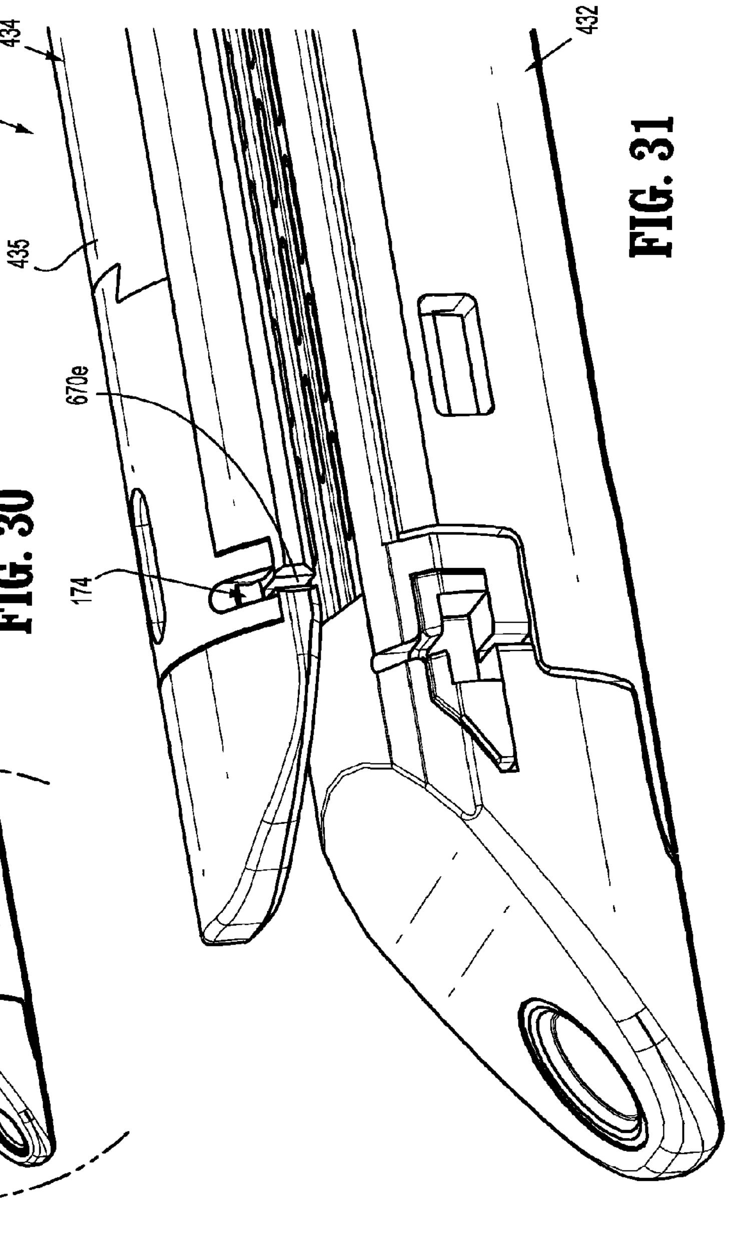
FIG. 31 is an enlarged view of the indicated area of detail of FIG. 31 according to the present disclosure.
Figure 32:
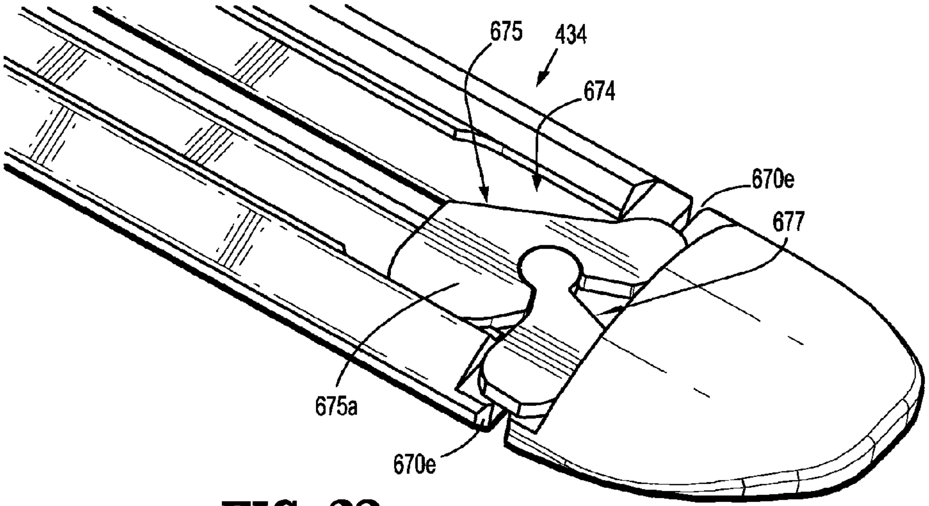
FIG. 32 is a top, perspective view of a distal end of an anvil assembly with an anvil cover removed, illustrating a suture release assembly thereof in an actuated configuration according to the present disclosure.
Figure 33:
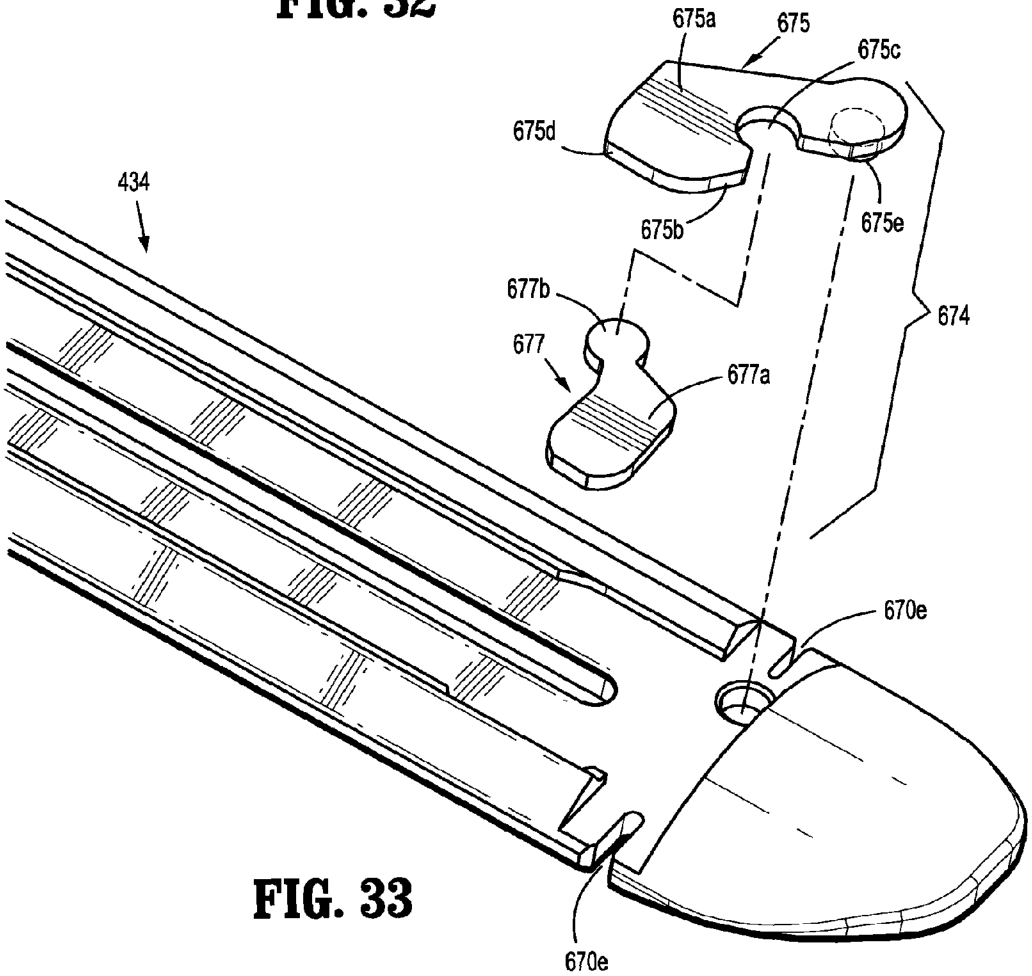
FIG. 33 is a top, perspective view of the distal end of the anvil assembly of FIG. 32, illustrating the parts of the suture release assembly thereof separated according to the present disclosure.

As seen in FIGS. 27 and 29, suture release assembly 594 includes an open or release configuration wherein finger 595*b* of anchor bar 595 does not extend into or overlie the respective one of the pair of distal recesses 432*b* in operative registration therewith, first cam surface 597*a* of actuation member 597 does not extend into and across central longitudinal slot 485 of cartridge assembly 432, and second cam surface 597*b* of actuation member 597 is not pressed against surface 432*g* of cartridge assembly 432.

Suture release assembly 594 may be used by a manufacturer during the assembly process of instrument 100 to secure, with an anchor, surgical suture, or tether "S", a surgical cartridge buttress "B2" (see FIG. 2) to a tissue contacting surface of the cartridge assembly 432, and by the end user of instrument 100 to automatically release or free the surgical cartridge buttress "B2" from the tissue contacting surface of the cartridge assembly 432 upon a complete firing of the instrument 100.

With reference to FIGS. 25-29, during the manufacturing process, with suture release assembly 594 in the open or release configuration, a surgical cartridge buttress "B2" is laid over the tissue contacting surface of cartridge assembly 432. Then, a first end of a surgical suture "S" is inserted into the relatively narrower of the pair of distal recesses 432*b* and a second end of surgical suture "S" is extended across the surgical cartridge buttress "B2" and inserted into the relatively wider of the pair of distal recesses 432*b*. It is contemplated that the first end of surgical suture "S" may include a knot, stop or the like (not shown) sized so as to not pass through the narrower recess of the distal pair of recesses 432*b*.

As seen in FIG. 26, cartridge assembly 432 includes an access opening 583 formed therein which is used to insert and receive suture release assembly 594 therein and to provide access to actuation member 597. With the second end of the surgical suture "S" disposed in the relatively wider of the pair of distal recesses 432*b*, and with the surgical suture "S" pulled taught across the surgical cartridge buttress "B2," actuation member 597 is rotated about the pivot axis causing first cam surface 597*a* of actuation member 597 to extend into and across central longitudinal slot 485 of cartridge assembly 432 and causing second cam surface 597*b* of actuation member 597 to press against surface 432*g* (see FIGS. 13 and 14) of cartridge assembly 432. In so doing, anchor bar 595 is pivoted by an amount sufficient for finger 595*b* of anchor bar 595 to extend into or overlies the respective one of the pair of distal recesses 432*b* in operative registration therewith thereby pinch the second end of the surgical suture disposed therewithin. Suture release assembly 594 is now in the locking or anchoring configuration, as described above.

In operation, with surgical cartridge buttress "B1" secured against the tissue contacting surface of cartridge assembly 432, during firing of instrument 100, as actuation sled 440 is advanced (i.e., moved from a proximal-most position to a distal-most position), knife blade 474 slices through a central section of the proximal suture "S4", thereby freeing the proximal end of the surgical cartridge buttress "B2" from cartridge assembly 432. During use, as the firing stroke of instrument 100 is nearing completion and as actuation sled 440 being driven by the drive screw 466 approaches a distal end of central longitudinal slot 485 of cartridge assembly 432, as seen in FIG. 29, actuation sled 440 contacts first cam surface 597*a* of actuation member 597, urging actuation member 597 to rotate. Second cam surface 597*b* of actuation member 597 also rotates about the pivot axis of pivot pin 595*c* thereof. As eccentric second cam surface 597*b* is rotated about the pivot axis second cam surface 597*b*, the distance between the pivot pin 595*c* and the surface 432*g* of cartridge assembly 432 is reduced thereby pivoting anchor bar 595 about pivot pin 595*c*. As anchor bar 595 is pivoted, finger 595*b* thereof is caused to move away from the relatively wider distal recess 432*b* and to release the second end of the surgical suture "S" disposed therewithin. With the second end of surgical suture "S" released or free, the distal end of the surgical cartridge buttress "B2" is free to separate from the tissue contacting surface of cartridge assembly 432. The distal recesses 432*b* that is in operative registration with finger 595*b* of anchor bar 595 is dimensioned so that, notwithstanding the rotation of anchor bar 595, the suture "S3" is not cinched therewithin.

As actuation sled 440 is advanced from the proximal position to the distal position, knife blade 474 thereof slices or cuts longitudinally through both surgical anvil buttress "B1" and surgical cartridge buttress "B2", thereby dividing the buttresses "B1, B2" substantially in half. Additionally, as actuation sled 440 is advanced from a proximal-most position to a distal-most position, upstanding cam wedges 444 of actuation sled 440 actuates pushers 437 to cause pushers 437 to translate vertically within retention slots and urge fasteners 433 from slots 446. As fasteners 433 are urged from slots 446 of cartridge assembly 432, legs of fasteners 433 penetrate and pass through both surgical anvil buttress "B1" and surgical cartridge buttress "B2", as well as any tissue interposed therebetween, and are formed against or within staple forming cavities of anvil 434 of anvil 434. Buttresses "B1, B2" may include perforations that divide the buttresses and facilitate removal of the apparatus from the tissue.

According to the present disclosure, surgical anvil buttress "B1" and/or surgical cartridge buttress "B2" is pre-loaded (i.e., from the manufacturer) onto anvil 434 or cartridge assembly 432, respectively, of the end effector 400. After the loading unit is fired, an additional unfired end effector 400 or the cartridge 432, with or without buttresses "B", can be loaded onto the instrument 100. A buttress and release assembly may be pre-loaded onto the removable cartridge and means for the user of the surgical apparatus to load a buttress onto the anvil assembly can be provided. For example, a buttress having an adhesive can be used. Additional or replacement buttresses "B" for anvil 434 and/or cartridge assembly 432 may be secured to either anvil 434 or cartridge assembly 432 as needed or desired.

In a further embodiment, the release assembly may be arranged to cut the suture "S." The cam surface 597*b* on the actuation member 597 may be arranged to cam the anchor bar 595 toward the suture "S." The surface of the anchor bar 595 that faces the suture "S" may include a sharpened edge and may cut the suture when actuated by the drive assembly.

As seen in FIGS. 30-35, another embodiment of the end effector 400 is shown. The anvil 434 of end effector 400 includes another embodiment of a suture release assembly 674 disposed between anvil 434 and anvil cover 435 at a location in operative registration with the distal pair of recesses 670*e*. Suture release assembly 674 includes a link arm 675 pivotally connected to anvil 434 (FIGS. 32 and 33) and/or optionally anvil cover 435. Link arm 675 includes a body portion 675*a* defining a pocket or recess 675*c* formed in a first side edge 675*b* thereof and a camming surface 675*d* defined substantially along an adjacent side or proximal edge thereof. Pocket 675*c* has a substantially arcuate, circular or rounded profile. As seen in FIGS. 18 and 20, link arm 675 includes a pivot pin 675*e* extending from body portion 675*a* for pivotally connecting link arm 675 to anvil 434.

Release assembly 674 further includes a pusher bar 677 pivotally connected to link arm 675 and slidably disposed between anvil 434 and anvil cover 435. Pusher bar 677 includes a body portion 677*a* having a substantially rectangular configuration and a head 677*b*, extending from a corner of body portion 677*a*, and having a substantially circular or rounded configuration. Head 677*b* of pusher bar 677 is configured and dimensioned for pivotable and/or rotatable connection in pocket 675*c* of link arm 675.

Figure 34:
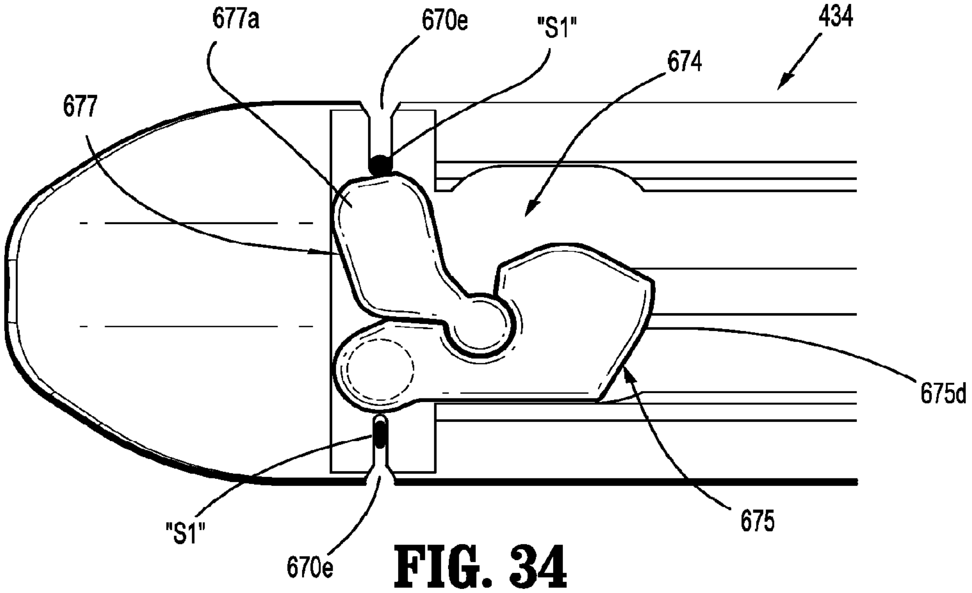
FIG. 34 is a top, plan view of the anvil assembly of FIG. 32, illustrating the suture release assembly thereof in an unactuated configuration according to the present disclosure.

As seen in FIG. 34, suture release assembly 674 includes an unactuated configuration wherein pusher bar 677 does not extend into or overlie the respective one of the pair of distal recesses 670*e* in operative registration therewith, and a longitudinal axis of link arm 675 is oriented substantially parallel with a longitudinal axis of end effector 400. It is contemplated that suture release assembly 674 may include a friction fit or snap fit feature for maintaining and/or retaining suture release assembly 674 in the locking or anchoring configuration at all times following the manufacturing/assembly process and prior to a complete firing of the surgical stapling apparatus.

Figure 35:
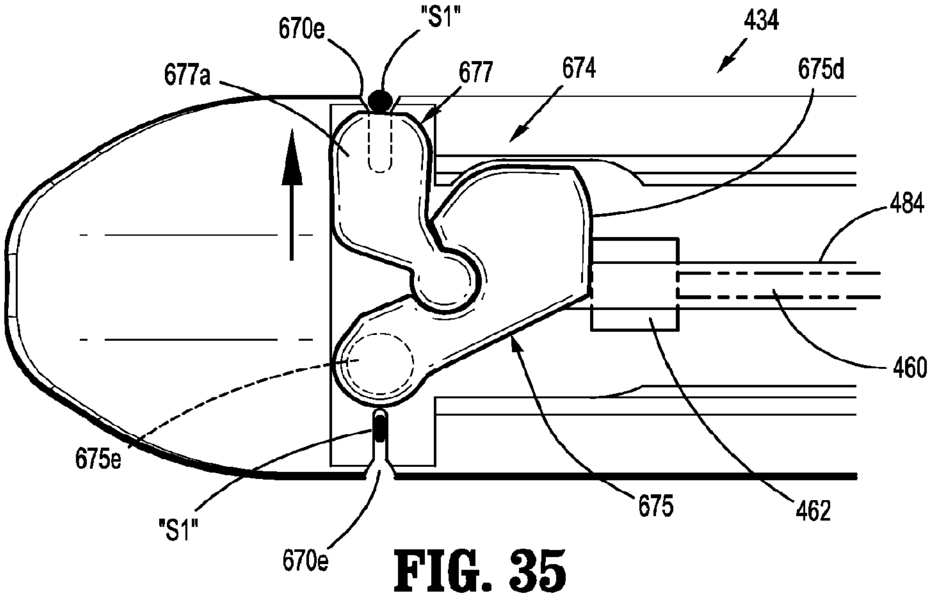
FIG. 35 is a top, plan view of the anvil assembly of FIG. 32, illustrating the suture release assembly thereof in an actuated configuration according to the present disclosure.
Figure 36:
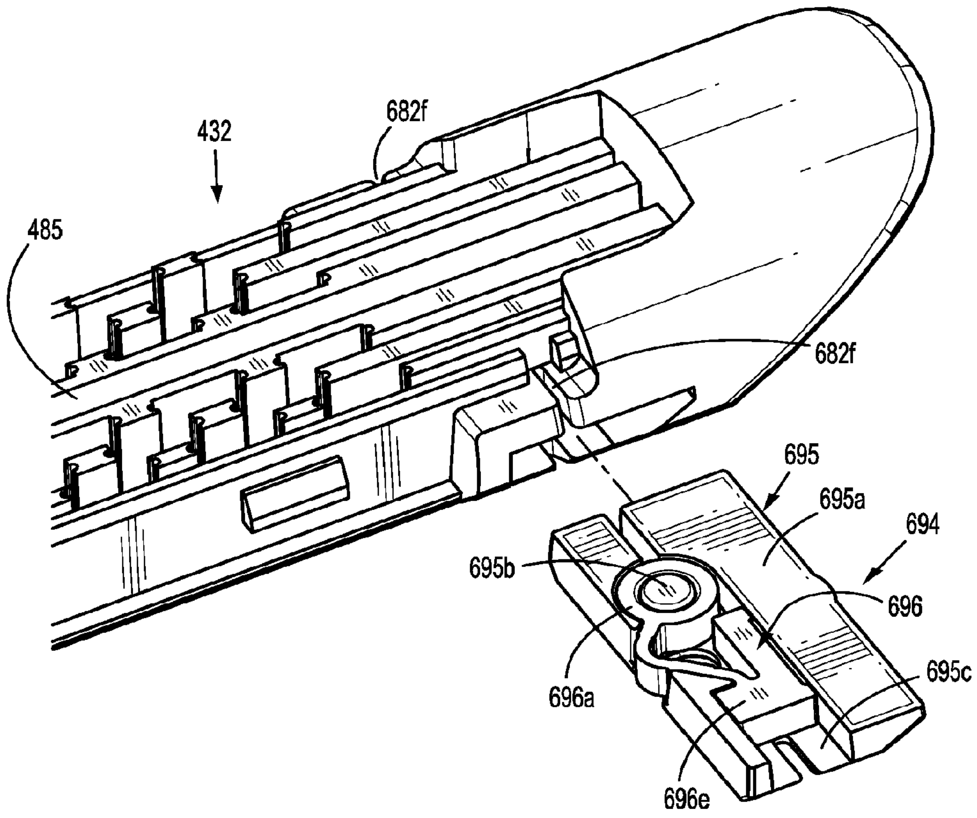
FIG. 36 is a bottom, perspective view of a distal end of a cartridge assembly of the end effector of FIG. 30, illustrating a suture release assembly thereof separated therefrom according to the present disclosure.
Figure 37:
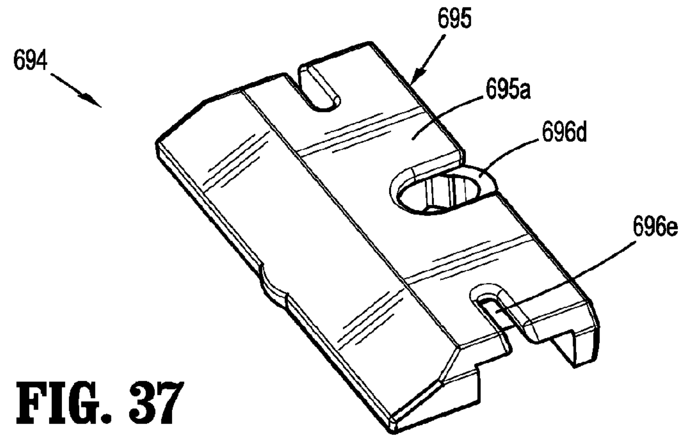
FIG. 37 is a top, perspective view of the suture release assembly of FIG. 36 according to the present disclosure.
Figure 38:
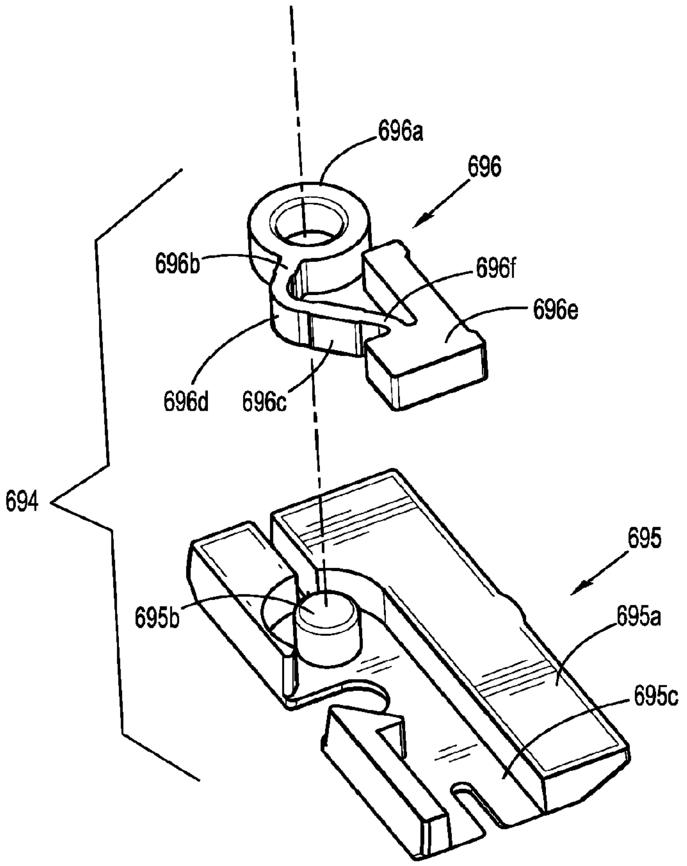
FIG. 38 is a bottom, perspective view, with parts separated, of the suture release assembly of FIG. 36 according to the present disclosure.

As seen in FIG. 35, suture release assembly 674 includes an actuated configuration wherein pusher bar 677 extends into or overlies the respective one of the pair of distal recesses 670*e* in operative registration therewith, and a longitudinal axis of link arm 675 is oriented substantially transverse to the longitudinal axis of end effector 400.

With reference to FIGS. 30-35, during the manufacturing process, with suture release assembly 674 in the unactuated configuration, a surgical anvil buttress (not shown) is laid over the tissue contacting surface of anvil 434. Then, a first end of a surgical suture "S1" is inserted into one of the pair of distal recesses 670*e* and a second end of surgical suture "S1" is extended across the surgical anvil buttress (not shown) and inserted into the other of the pair of distal recesses 670*e*. It is contemplated that each of the pair of distal recesses 670*e* is an open ended constricting slot so as to frictionally grip or cinch a surgical suture "S1" disposed therein.

In operation, with a surgical anvil buttress (not shown) secured against the lower surface of anvil 434, during firing of the surgical stapling apparatus, as the drive beam 462 being driven by the draft screw 460 is advanced (i.e., moved from a proximal-most position to a distal-most position), knife blade 474 slices through a central section of the proximal suture (not shown), thereby freeing the proximal end of the surgical anvil buttress (not shown) from anvil 434. During use, as the firing stroke of the surgical stapling apparatus is nearing completion and as the drive beam approaches a distal-most end of longitudinal slot 484 of anvil 434, as seen in FIG. 35, drive beam 462 contacts camming surface 675*d* of link arm 675, thus urging link arm 675 to rotate or pivot around the pivot pin and, in turn, urging pusher bar 677 to translate in the direction of the slot. As pusher bar 677 is translated, pusher bar 677 comes into contact with and urges the second end of suture "S1" out of the distal recess 670*e* that is registration therewith to release the second end of suture "S1" therefrom. With the second end of surgical suture "S1" released or free from distal recess 670*e*, the distal end of the surgical anvil buttress "B1" is free to separate from the tissue contacting surface of anvil 434.

As seen in FIGS. 30, 31 and 36-40, cartridge assembly 432 of end effector 400 includes a cartridge release assembly 694 supported in and near a distal end thereof. Release assembly 694 includes a retainer 695 supported in a distal end of the cartridge assembly 432 at a location near a distal end of longitudinal slot 485 and at least partially extending thereacross. Retainer 695 includes a body portion 695*a*, a boss 695*b* extending from a surface thereof, and defines a channel or recess 695*c* formed in a surface thereof and extending through a side thereof. When supported in cartridge assembly 432, recess 695*c* of retainer 695 is in registration with one of the pair of distal recesses 682*f* of cartridge assembly 432.

Release assembly 694 further includes a pusher member 696 having a head portion 696*a* pivotally connected to boss 695*b* of retainer 695. Pusher member 696 further includes a first leg member 696*b* extending from head portion 696*a* and a second leg member 696*c* connected to a free end of first leg member 696*b* via a living hinge connection 696*d*. Pusher member 696 further includes piston 696*e* connected to a free end of second leg member 696*c* via a living hinge connection 696*f*. Piston 696*e* is slidably disposed and translatable within recess 695*c* of retainer 695. In certain other embodiments, the pusher is a linkage assembly having a first link pivotably connected to the cartridge at one end. The other end of the first link is pivotably connected to a first end of a second link. The opposite, second, end of the second link is confined in the recess of the retainer.

Figure 39:
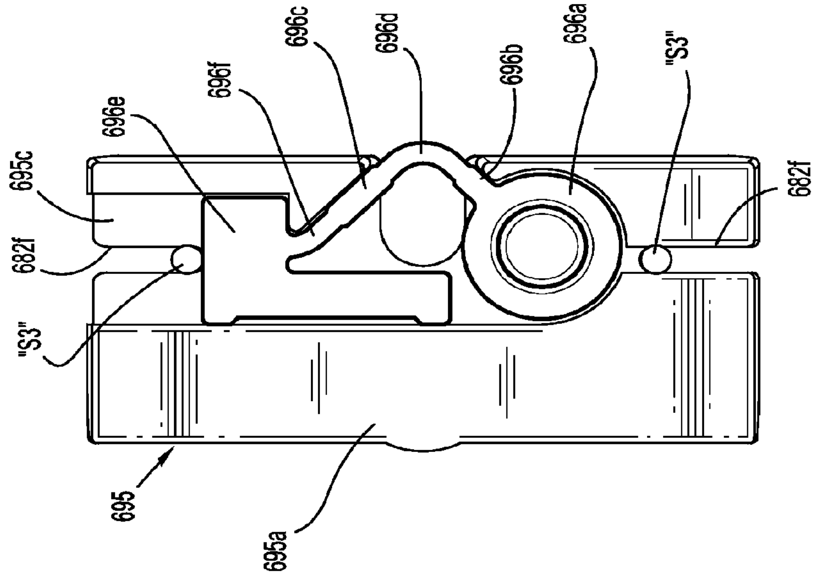
FIG. 39 is a top, plan view of the suture release assembly of FIG. 36, illustrating the suture release assembly thereof in an unactuated configuration according to the present disclosure.

As seen in FIG. 39, release assembly 694 includes an unactuated configuration wherein piston 696*e* does not extend into or overlie the respective one of the pair of distal recesses 682*f*, and first leg member 696*b* and second leg member 696*c* are angled with respect to one another and project proximally along longitudinal slot 485 of cartridge assembly 432. It is contemplated that suture release assembly 694 may include a friction fit or snap fit feature for maintaining and/or retaining suture release assembly 694 in the locking or anchoring configuration at all times following the manufacturing/assembly process and prior to a complete firing of the surgical stapling apparatus.

Figure 40:
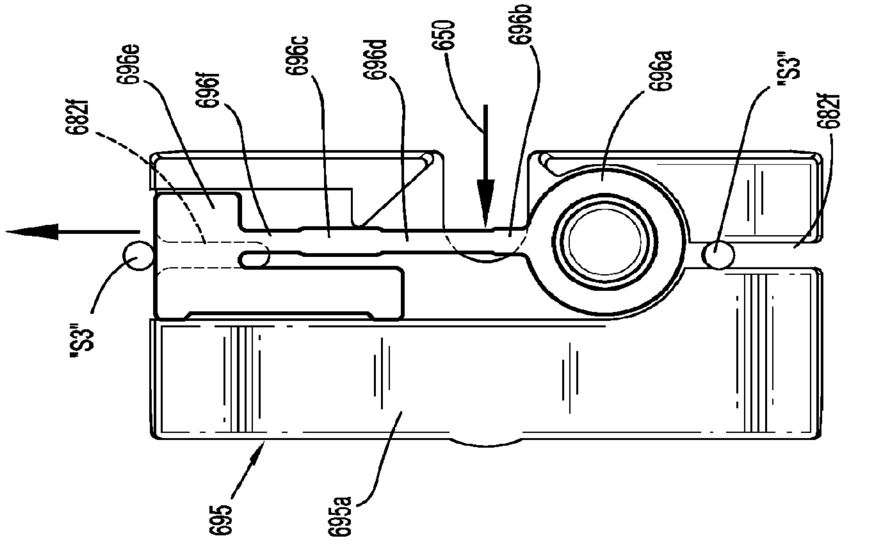
FIG. 40 is a top, plan view of the suture release assembly of FIG. 36, illustrating the suture release assembly thereof in an actuated configuration according to the present disclosure.

As seen in FIG. 40, suture release assembly 694 also includes an actuated configuration wherein piston 696*e* extends into or overlies the respective one of the pair of distal recesses 682*f* in operative registration therewith, and first leg member 696*b* and second leg member 696*c* are extended substantially along a common axis.

With reference to FIGS. 36-40, during the manufacturing process, with suture release assembly 694 in the unactuated configuration, a surgical cartridge buttress (not shown) is laid over the tissue contacting surface of cartridge assembly 432. Then, a first end of a surgical suture "S3" is inserted into one of the pair of distal recesses 682*f* and a second end of surgical suture "S3" is extended across the surgical cartridge buttress and inserted into the other of the pair of distal recesses 682*f*. It is contemplated that at least the recess 682*f* that is adjacent the retainer 695 is an open ended constricting slot so as to frictionally grip or cinch a surgical suture "S3" disposed therein.

In operation, with surgical cartridge buttress (not shown) secured against the tissue contacting surface of cartridge assembly 432, during firing of surgical stapling instrument 100, as the actuation sled 440 being driven by the drive screw 466 is advanced (i.e., moved from a proximal-most position to a distal-most position), knife blade 474 slices through a central section of a proximal suture (not shown), thereby freeing the proximal end of the surgical cartridge buttress from cartridge assembly 432. During use, as the firing stroke of surgical stapling instrument 100 is nearing completion and as the actuation sled 440 being driven by the drive screw 466 approaches a distal end of central longitudinal slot 485 of cartridge assembly 432, as seen in FIG. 29, drive the actuation sled 440 contacts living hinge connection 696*d* between first leg member 696*b* and second leg member 696*c*. As the actuation sled 440 is further advanced distally, the actuation sled

440 presses against living hinge connection 696*d*, causing first leg member 696*b* and second leg member 696*c* to extend. As first leg member 696*b* and second leg member 696*c* extend, piston 696*e* is translated through recess 695*c* of retainer 695. As piston 696*e* is translated through recess 695*c* of retainer 695, piston 696*e* engages the second end of suture "S3" and urges suture "S3" out of the distal recess 682*f* that is registration therewith to release the second end of suture "S3" therefrom. With the second end of surgical suture "S3" released or free from distal recess 682*f*, the distal end of the surgical cartridge buttress "B" is free to separate from the tissue contacting surface of cartridge assembly 432.

According to further embodiments of the present disclosure, it is contemplated that buttresses "B" may be provided or formed with integral wings or tabs extending therefrom for insertion and/or receipt into distal and/or proximal recesses of anvil assembly and/or cartridge assembly. It is further contemplated that sutures "S" may be affixed to, embedded in or other wise connected to buttresses "B."

Exemplary surgical buttresses "B" for use with the surgical stapling devices disclosed herein are shown and described in commonly assigned U.S. Pat. Nos. 5,542,594; 5,908,427; 5,964,774; and 6,045,560, and commonly assigned U.S. application Ser. No. 12/579,605, filed on Oct. 15, 2009 (now U.S. Patent Publication No. 2010/0092710), commonly assigned U.S. application Ser. No. 11/241,267, filed on Sep. 30, 2005 (now U.S. Patent Publication No. 2006/0085034), and U.S. application Ser. No. 11/248,846, filed on Oct. 12, 2005 (U.S. Patent Publication No. 2006/0135992, now U.S. Pat. No. 7,823,592), the entire contents of each of which is incorporated herein by reference.

Surgical buttresses "B" may be fabricated from a suitable biocompatible and bioabsorbable material. Surgical buttresses "B" may be fabricated from a non-absorbent material which does not retain fluid. Surgical buttresses "B" may be fabricated from "BIOSYN" made from GLYCOMER 631 (a block copolymer), a synthetic polyester composed of glycolide, dioxanone and trimethylene carbonate.

One block of the resulting copolymer contains randomly combined units derived from p-dioxanone (1,4-dioxan-2-one) and trimethylene carbonate (1,3-dioxan-2-one). The second block of the copolymer contains randomly combined units derived from glycolide and p-dioxanone. The resulting polyester is an ABA triblock terpolymer possessing about 60% glycolide, about 14% dioxanone, and about 26% trimethylene carbonate.

It will be understood that various modifications may be made to the embodiments disclosed herein. For example, the instrument 100 need not apply staples but rather may apply two part fasteners as is known in the art. Further, the length of the linear row of staples or fasteners may be modified to meet the requirements of a particular surgical procedure. Thus, the length of a single stroke of the actuation shaft and/or the length of the linear row of staples and/or fasteners within a disposable loading unit may be varied accordingly. Therefore, the above description should not be construed as limiting, but merely as exemplifications of preferred embodiments. Those skilled in the art will envision other modifications within the scope and spirit of the claims appended thereto.

The invention claimed is:

1. A surgical system, comprising:

a handle housing including a rotatable actuation shaft;

an elongated body including a flexible portion and a flexible drive shaft in the flexible portion, the elongated body couplable to the handle housing such that the flexible drive shaft couples to the actuation shaft; and a jaw assembly couplable to the elongated body, the jaw assembly including:

first and second jaws, the second jaw defining a cam surface and pivotally movable relative to the first jaw from an open position to a closed position;

a drive beam including a cam member positioned to engage the cam surface of the second jaw member, the drive beam longitudinally movable through the first and second jaw members such that the cam member is translated along the cam surface of the second jaw to move the first and second jaws from the open position to the closed position; and a drive screw supported within the first jaw, the drive screw including a threaded portion threadably coupled to the drive beam, the drive screw coupled to the flexible drive shaft configured to transfer rotational motion of the actuation shaft to the drive screw, such that rotation of the drive screw imparts longitudinal movement of the drive beam.

2. The surgical system according to claim 1, wherein the first jaw includes a removable cartridge assembly including a plurality of fasteners.

3. The surgical system according to claim 2, wherein the second jaw includes an anvil having a fastener forming surface thereon.

4. The surgical system according to claim 3, wherein the jaw assembly further includes an actuation sled supported within the cartridge assembly, the actuation sled being movable to urge the plurality of fasteners from the cartridge assembly.

5. The surgical system according to claim 4, wherein the drive beam abuts the actuation sled such that during longitudinal movement of the drive beam the actuation sled is pushed through the cartridge assembly to urge the plurality of fasteners from the cartridge assembly.

6. The surgical system according to claim 1, wherein the flexible portion includes a plurality of interlocking segments.

7. The surgical system according to claim 1, further comprising a drive link interconnecting the flexible drive shaft and the drive screw, wherein the drive screw defines a first longitudinal axis and the flexible drive shaft defines a second longitudinal axis, and wherein the drive link is disposed off-axis in relation to the first and second longitudinal axes.

8. The surgical system according to claim 7, wherein the drive link includes a proximal engagement portion mechanically coupled to the flexible drive shaft and a distal engagement portion mechanically coupled to the drive screw.

9. The surgical system according to claim 8, wherein the proximal engagement portion includes a socket configured and dimensioned to mechanically interface with a ball joint disposed at a distal end of the flexible drive shaft.

10. The surgical system according to claim 8, wherein the distal engagement portion includes a pin configured and dimensioned to mechanically interface with a clevis disposed at a proximal end of the drive screw.

11. The surgical system according to claim 1, further comprising:

a surgical buttress releasably secured to a tissue contacting surface of at least one of the first jaw or the second jaw; and a release assembly disposed within at least one of the first jaw or the second jaw.

12. The surgical system according to claim 11, wherein the drive screw is configured to actuate the release assembly to thereby release the surgical buttress from the at least one of the first jaw or the second jaw.

13. The surgical system according to claim 1, wherein the handle housing further includes a control assembly configured to accept at least one user input.

14. The surgical system according to claim 13, wherein the handle housing further includes a first motor and a second motor configured to operate in response to the at least one user input.

15. The surgical system according to claim 14, wherein the handle housing further includes a power source configured to provide electrical energy to the first and second motors.

16. The surgical system according to claim 14, wherein the handle housing further includes a selector gearbox assembly comprising at least one gear element mechanically coupled to the flexible drive shaft, wherein the first motor is configured to selectively move the at least one gear element into engagement with the second motor to actuate the flexible drive shaft.

17. A surgical system, comprising:

an elongated body including a flexible portion and a flexible drive shaft in the flexible portion, the flexible drive shaft defining a first longitudinal axis; and a jaw assembly couplable to the elongated body, the jaw assembly including:

first and second jaws, the second jaw defining a cam surface and pivotally movable relative to the first jaw from an open position to a closed position;

a drive beam including a cam member positioned to engage the cam surface of the second jaw member, the drive beam longitudinally movable through the first and second jaw members such that the cam member is translated along the cam surface of the second jaw to move the first and second jaws from the open position to the closed position;

a drive screw supported within the first jaw, the drive screw defining a second longitudinal axis and including a threaded portion threadably coupled to the drive beam; and a drive link interconnecting the flexible drive shaft and the drive screw, wherein the drive link is disposed off-axis in relation to the first and second longitudinal axes, the drive link configured to transfer rotational motion of the flexible drive shaft to the drive screw, such that rotation of the drive screw imparts longitudinal movement of the drive beam.

18. The surgical system according to claim 17, wherein the first jaw includes a removable cartridge assembly having a plurality of fasteners and the second jaw includes an anvil having a fastener forming surface thereon.

19. The surgical system according to claim 18, wherein the jaw assembly further includes an actuation sled supported within the cartridge assembly, the actuation sled being movable to urge the plurality of fasteners from the cartridge assembly.

20. The surgical system according to claim 19, wherein the drive beam abuts the actuation sled such that during longitudinal movement of the drive beam the actuation sled is pushed through the cartridge assembly to urge the plurality of fasteners from the cartridge assembly.

* * * * *